United States Patent
Lee et al.

(10) Patent No.: US 7,892,534 B2
(45) Date of Patent: Feb. 22, 2011

(54) DIFFERENTIATING HUMAN TROPHOBLAST STEM CELLS IN MAMMALIAN STRAITUM

(76) Inventors: Jau-Nan Lee, No. 1 Nan Shin Chen Street, Kaohsiung (TW); Tony Tung-Ying Lee, No. 1 Nan Shin Chen Street, Kaohsiung (TW); Yuta Lee, No. 1 Nan Shin Chen Street, Kaohsiung (TW)

( * ) Notice: Subject to any disclaimer, the term of this patent is extended or adjusted under 35 U.S.C. 154(b) by 51 days.

(21) Appl. No.: 12/405,112

(22) Filed: Mar. 16, 2009

(65) Prior Publication Data

US 2009/0263361 A1  Oct. 22, 2009

Related U.S. Application Data

(62) Division of application No. 11/361,588, filed on Feb. 24, 2006, now Pat. No. 7,642,091.

(60) Provisional application No. 60/655,747, filed on Feb. 24, 2005.

(51) Int. Cl.
*A01N 63/00* (2006.01)
*A01N 65/00* (2006.01)

(52) U.S. Cl. .................... 424/93.7; 424/93.1

(58) Field of Classification Search ........... None
See application file for complete search history.

(56) References Cited

U.S. PATENT DOCUMENTS

| | | |
|---|---|---|
| 6,630,349 B1 | 10/2003 | Rossant et al. |
| 2004/0072288 A1 | 4/2004 | Collas et al. |
| 2006/0211110 A1 | 9/2006 | Lee et al. |

OTHER PUBLICATIONS

Qureshi, et al. Anti-DNA antibodies cross-reacting with laminin inhibit trophoblast attachment and migration: implications for recurrent pregnancy loss in SLE patients. Am J Reprod Immunol. Sep. 2000;44(3):136-42.
Arnit, et al. Clonally Derived Human Embryonic Stem Cell Lines Maintain Pluripotency and Proliferative Potential for Prolonged Periods of Culture, Developmental Biology 227,271-278 (2000).
Chai, et al. FGF Is an Essential Regulator of the Fifth Cell Division in Preimplantation Mouse Embryos, Development Biology, vol. 198, pp. 105-115 (1998).
Cheng, et al. Human Adult Marrow Cells Support Prolonged Expansion of Human Embryonic Stem Cells in Culture, Stem Cells, vol. 21 pp. 131-142 (2003).
Copp, A.J. Interaction between inner cell mass and trophectoderm of the mouse blastocyst, J. Embryol. Exp. Morph., vol. 51, pp. 109-120 (1979).
Gerami-Naini, et al. Trophoblast Differentiation in Embryoid Bodies Derived from Human Embryonic Stem Cells, Endocrinology, vol. 145(4) p. 1517-1524 (2004).
Iancu, et al. Behavioral characterization of a unilateral 6-OHDA-lesion model of Parkinson's disease in mice, Behavioural Brain Research, vol. 162 pp. 1-10 (2005).
Kehler, et al. Oct. 4 is required for primordial germ cell survival, European Molecular Biology Organization reports, vol. 5 No. 1 1, pp. 1078-1083 (2004).
Kunath, et al. Trophoblast Stem Cells, Stem Cell Biology, pp. 267-287, (2001).
Nichols, et al. Formation of Pluripotent Stem Cells in the Mammalian Embryo Depends on the POU Transcription Factor Oct. 4, Cell, vol. 95, pp. 379-391 (1998).
Rossant, et al. Effect of culture conditions on diploid to giant-cell transformation in postimplantation mouse trophoblast, J. Embryol. exp. Morph., vol. 62, pp. 217-227, (1981).
Rossant, J. Stem Cells from the Mammalian Blastocyst, Stem Cells, vol. 19, pp. 477-482 (2001).
Schulz, et al. Human embryonic stem cells as models for trophoblast differentiation. Placenta. Mar. 2008;29 Suppl A:S10-6.
Shamblott, et al. Derivation of pluripotent stem cells from cultured human primordial germ cells, Proc. Natl. Acad. Sci. USA, vol. 95, pp. 13726-13731 (1998).
Shamblott, et al. Human embryonic germ cell derivatives express a broad range of developmentally distinct markers and proliferate extensively in vitro, Proc. Natl. Acad. Sci., vol. 98 No. 1, pp. 113-118 (2001).
Thornson, et al. Embroynic Stem Cell Lines Derived from Human Blastocysts, Science, vol. 282 pp. 1145-1147 (1998).
Xu, et al. BMP4 initiates human embryonic stem cell differentiation to trophoblast. Nat Biotechnol. Dec. 2002;20(12):1261-4.
Xu, R. In vitro induction of trophoblast from human embryonic stem cells. Methods Mol Med. 2006;121:189-202.
International Search Report mailed Nov. 23, 2007 in connection with PCT/US2006/006512, Applicant Lee, et al.
Written Opinion mailed Nov. 23, 2007 in connection with PCT/US2006/006512, Applicant Lee, et al.
International Preliminary Report on Patentability mailed Nov. 23, 2007 in connection with PCT/US2006/006512, Applicant Lee, et al.

*Primary Examiner*—Robert M Kelly
(74) *Attorney, Agent, or Firm*—Wilson, Sonsini, Goodrich & Rosati, PC

(57) ABSTRACT

Existence of human trophoblast stem (hTS) cells has been suspected but unproved. The isolation of hTS cells is reported in the early stage of chorionic villi by expressions of FGF4, FGFR-2, Oct4, Thy-1, and stage-specific embryonic antigens distributed in different compartments of the cell. hTS cells are able to derive into specific cell phenotypes of the three primitive embryonic layers, produce chimeric reactions in mice, and retain a normal karyotype and telomere length. In hTS cells, Oct4 and fgfr-2 expressions can be knockdown by bFGF. These facts suggest that differentiation of the hTS cells play an important role in implantation and placentation. hTS cells could be apply to human cell differentiation and for gene and cell-based therapies.

15 Claims, 13 Drawing Sheets

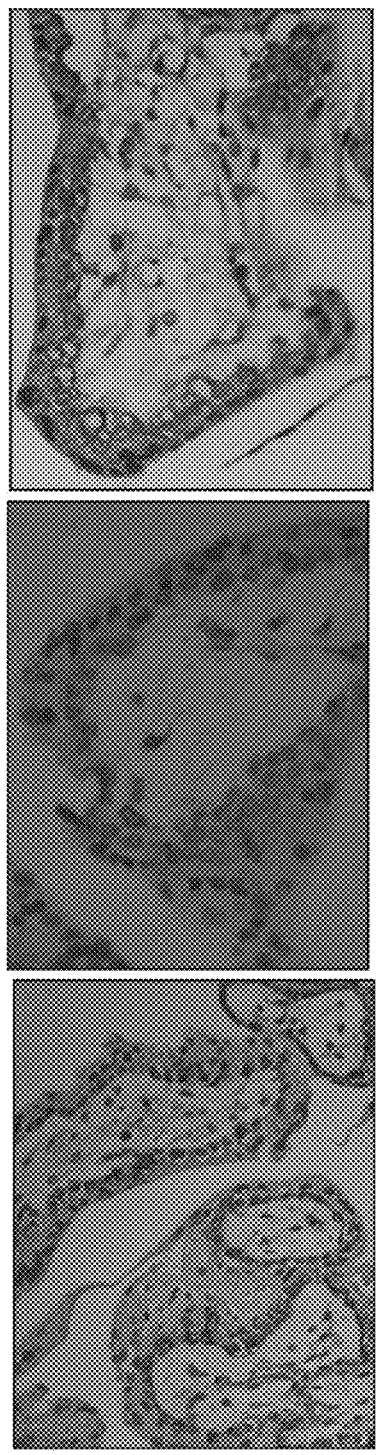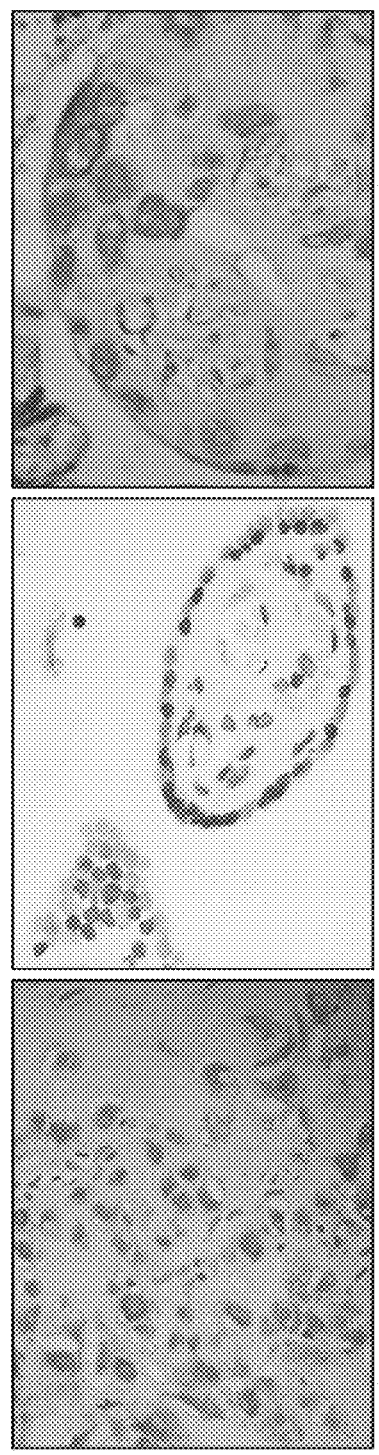

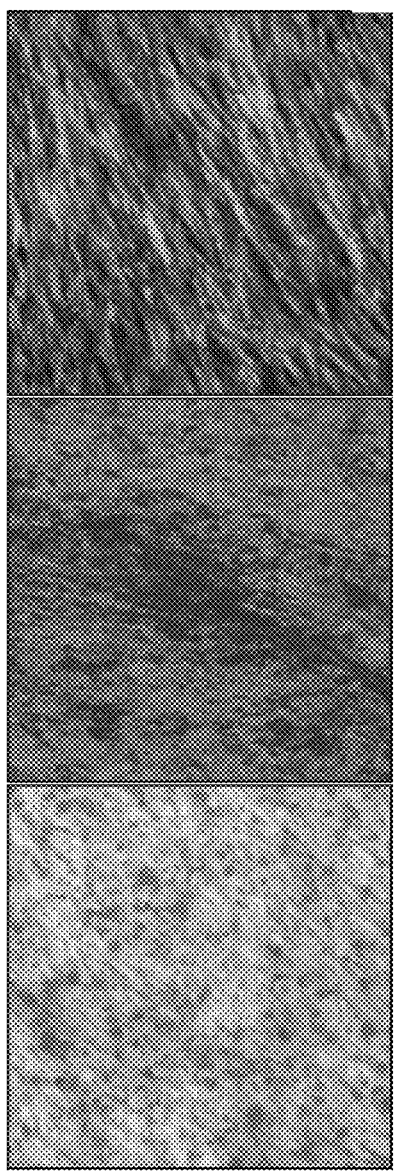
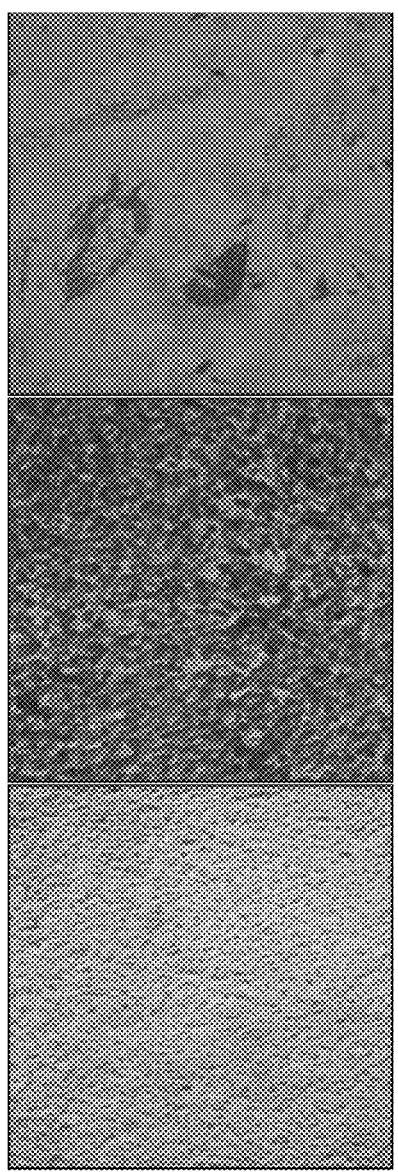
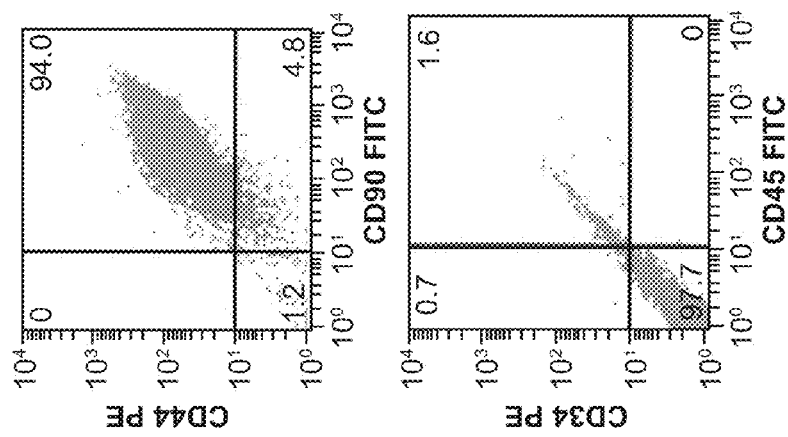

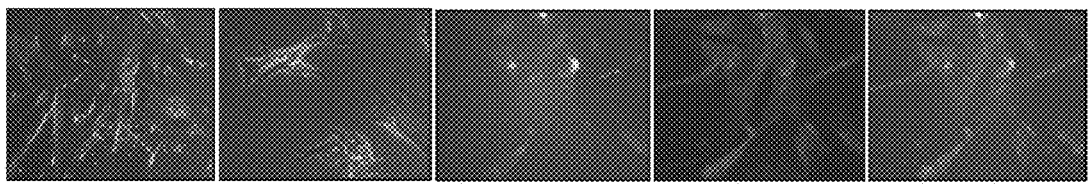
FIG. 4A  FIG. 4B  FIG. 4C  FIG. 4D  FIG. 4E
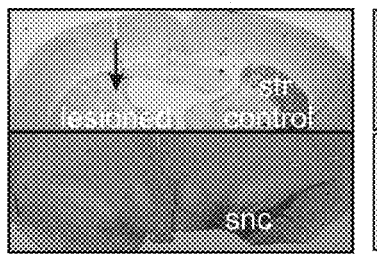 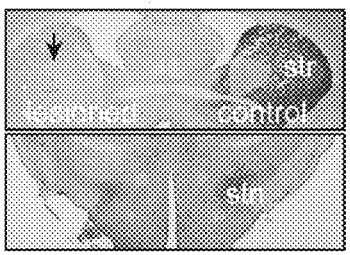 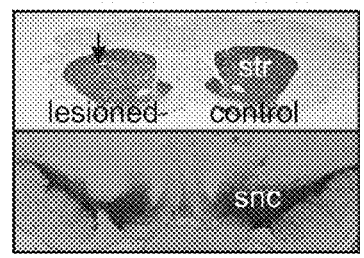
FIG. 4F        FIG. 4G        FIG. 4H
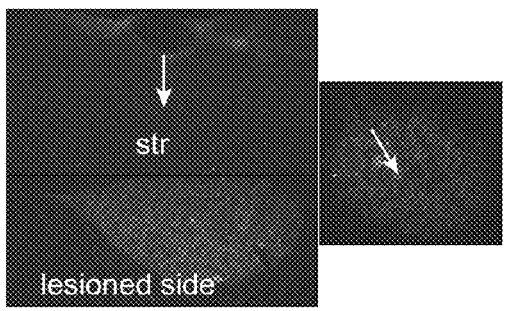 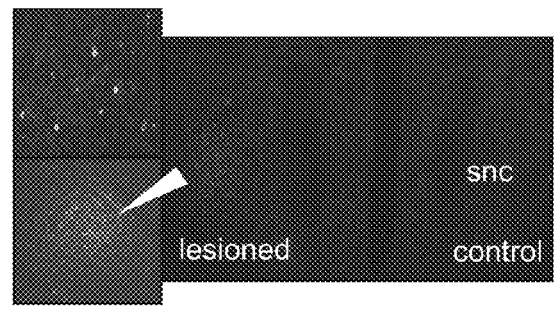
FIG. 4I        FIG. 4J
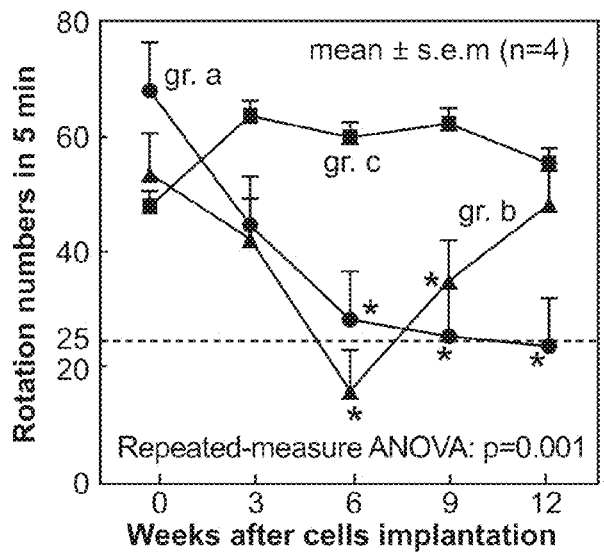
FIG. 4K

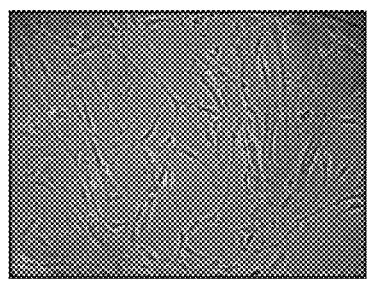
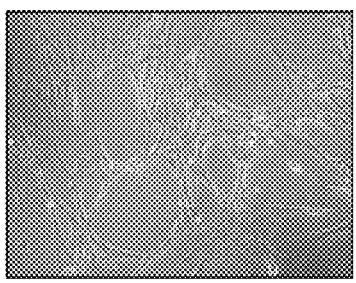
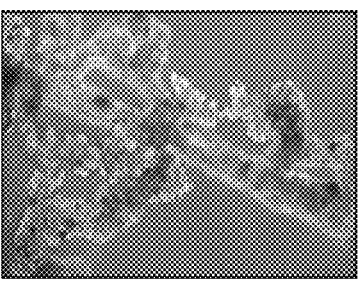
FIG. 5A          FIG. 5B          FIG. 5C
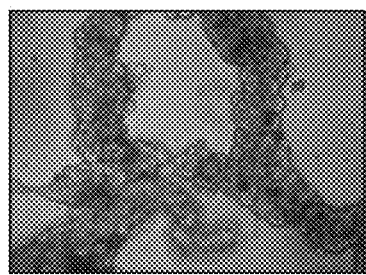
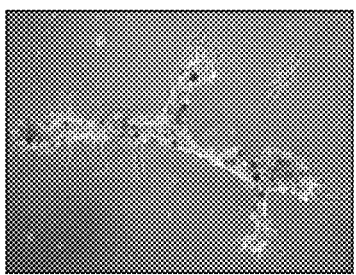
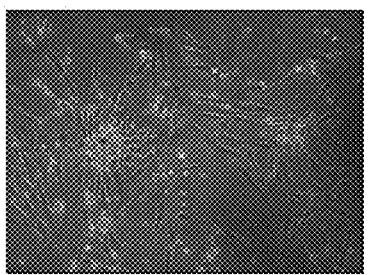
FIG. 5D          FIG. 5E          FIG. 5F
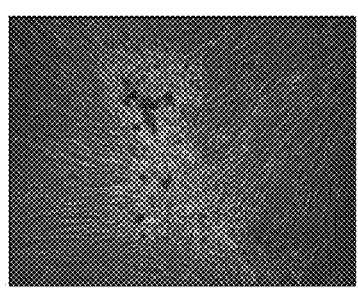
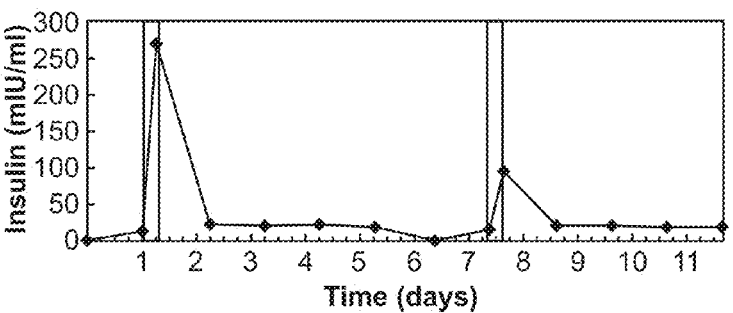
FIG. 5G          FIG. 5H

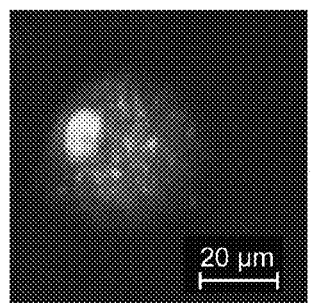 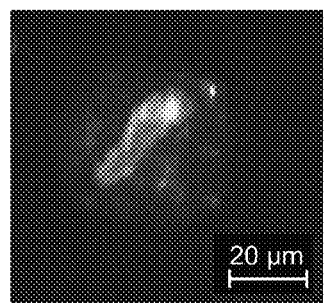 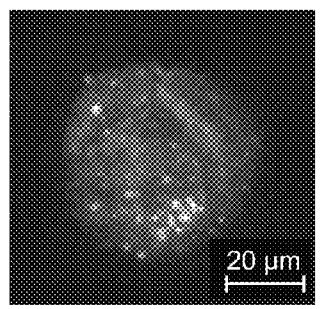
FIG. 7A  FIG. 7B  FIG. 7C
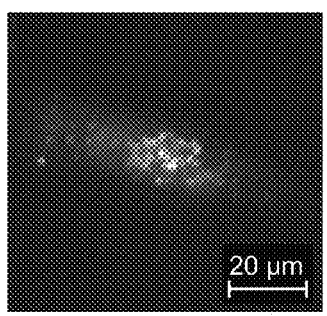 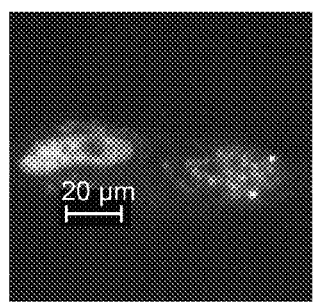 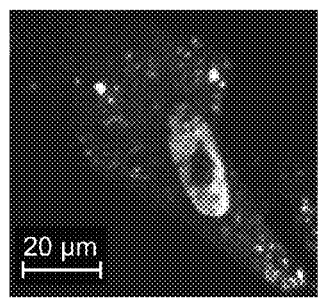
FIG. 7D  FIG. 7E  FIG. 7F

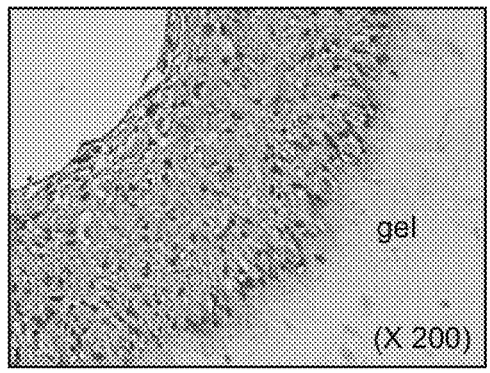
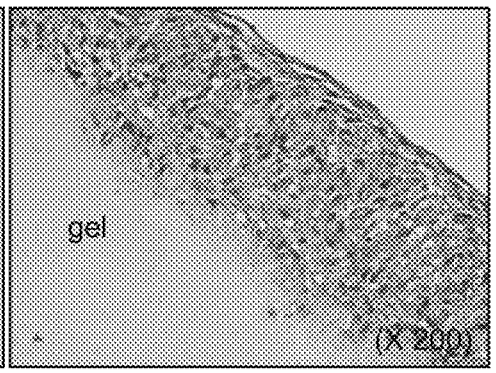
FIG. 9A  FIG. 9B
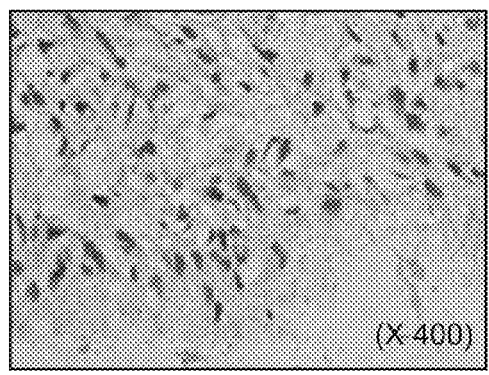
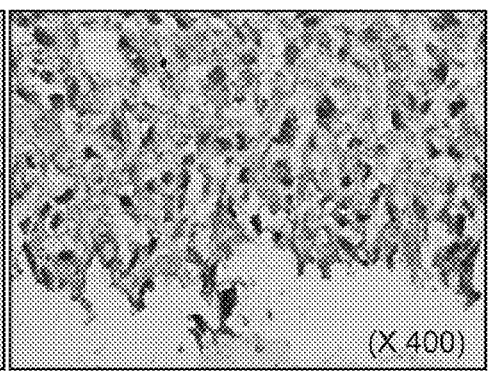
FIG. 9C  FIG. 9D
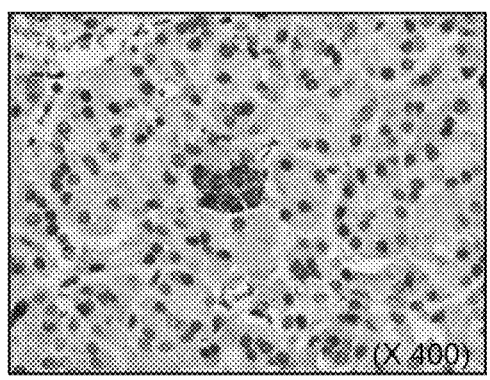
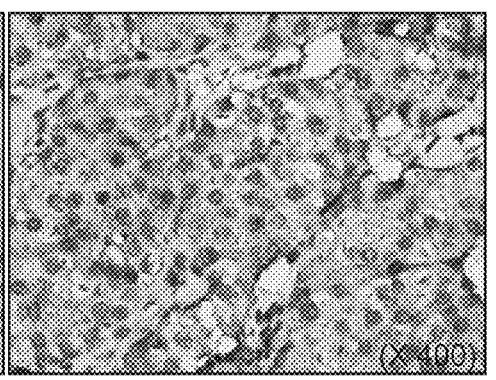
FIG. 9E  FIG. 9F ary application of U.S. patent
DIFFERENTIATING HUMAN TROPHOBLAST STEM CELLS IN MAMMALIAN STRAITUM

CROSS REFERENCE

The application is a divisional application of U.S. patent application Ser. No. 11/361,588, filed on Feb. 24, 2006, now U.S. Pat. No. 7,642,091, which claims priority to U.S. Provisional Application Ser. No. 60/655,747, filed on Feb. 24, 2005.

BACKGROUND OF THE INVENTION

1. Field of the Invention

This invention relates to an isolated preparation of human trophoblast stem cells and use thereof.

2. Description of the Related Art

In mammals, the earliest developmental decision specifies the trophoblast cell lineage. In mice, this lineage appears at the blastocyst stage as the trophectoderm, a sphere of epithelial cells surrounding the inner cell mass (ICM) and the blastoceol. After implantation, the ICM gives rise to the embryo proper and some extraembryonic membranes. However, the trophectoderm is exclusively restricted to form the fetal portion of the placenta and the trophoblast giant cells. The polar trophectoderm (the subset of trophectoderm in direct contact with the ICM) maintains a proliferative capacity and gives rise to the extraembryonic ectoderm (ExE), the ectoplacental cone (EPC), and secondary giant cells of the early conceptus. The rest of the trophectoderm ceases to proliferate and becomes primary giant cells. Studies in primary culture and chimeric mice have suggested that stem cells exist in the extraembryonic ectoderm which contribute descendants to the EPC and the polyploid giant cells. Further evidence indicated that maintenance of these stem cell-like characteristics was dependent on signals from the ICM and later from the epiblast, since diploid trophoblast cells transformed into giant cells when removed from the embryonic environment. However, the nature of the embryo-derived signal was not known and all attempts at routine long-term culture of mouse trophoblast stem cells have been unsuccessful (U.S. Pat. No. 6,330,349).

Stem cells have the capacity to divide and proliferate indefinitely in culture. Scientists use these two properties of stem cells to produce seemingly limitless supplies of most human cell types from stem cells, paving the way for the treatment of diseases by cell replacement. In fact, cell therapy has the potential to treat any disease that is associated with cell dysfunction or damage including stroke, diabetes, heart attack, spinal cord injury, cancer and AIDS. The potential of manipulation of stem cells to repair or replace diseased or damaged tissue has generated a great deal of excitement in the scientific, medical and/biotechnology investment communities.

U.S. Appl. No. 2003104616 disclosures that ES cells from various mammalian embryos have been successfully grown in the laboratory. Evans and Kaufman (1981) and Martin (1981) showed that it is possible to derive permanent lines of embryonic cells directly from mouse blastocysts. Thomson et al., (1995 and 1996) successfully derived permanent cell lines from rhesus and marmoset monkeys. Pluripotent cell lines have also been derived from pre-implantation embryos of several domestic and laboratory animal species such as bovines (Evans et al., 1990) Porcine (Evans et al., 1990, Notarianni et al., 1990), Sheep and goat (Meinecke-Tillmann and Meinecke, 1996, Notarianni et al., 1991), rabbit (Giles et al., 1993, Graves et al., 1993) Mink (Sukoyan et al., 1992) rat (Iannaccona et al., 1994) and Hamster (Doetschman et al., 1988). Recently, Thomson et al (1998) and Reubinoff et al (2000) have reported the derivation of human ES cell lines. These human ES cells resemble the rhesus monkey ES cell lines.

ES cells are found in the ICM of the human blastocyst, an early stage of the developing embryo lasting from the $4^{th}$ to $7^{th}$ day after fertilization. The blastocyst is the stage of embryonic development prior to implantation that contains two parts via.

1. Trophectoderm: outer layer which gives extra embryonic membranes.

2. Inner cell mass (ICM): which forms the embryo proper.

In normal embryonic development, ES cells disappear after the $7^{th}$ day and begin to form the three embryonic tissue layers. ES cells extracted from the ICM during the blastocyst stage, however, can be cultured in the laboratory and under the right conditions proliferate indefinitely. ES cells growing in this undifferentiated state retain the potential to differentiate into cells of all three embryonic tissue layers. Ultimately, the cells of the inner cell mass give rise to all the embryonic tissues. It is at this stage of embryogenesis, near the end of first week of development, that ES cells can be derived from the ICM of the blastocyst.

The ability to isolate ES cells from blastocyst and grow them in culture seems to depend in large part on the integrity and condition of the blastocyst from which the cells are derived. In short, the blastocyst that is large and has distinct inner cell mass tend to yield ES cells most efficiently. Several methods have been used for isolation of inner cell mass (ICM) for the establishment of embryonic stem cell lines. Most common methods are natural hatching of the blastocyst, microsurgery and immunosurgery.

Expression and functional analyses indicated that FGF4 and fgfr-2 may be involved in trophoblast proliferation. The reciprocal expression domains of fgfr-2 and FGF4 suggested that the trophoblast could be a target tissue for an embryonic FGF signal. fgfr-2-null and FGF4-null mice show similar peri-implantation lethal phenotypes. This may result from defects in the ICM and its endoderm derivatives. However, it is also consistent with the possibility that FGF4 acts on the trophoblast through fgfr-2 to maintain a proliferating population of trophoblast cells. Support for this latter possibility is provided by recent studies showing that inhibiting FGF signaling blocked cell division in both the ICM and trophectoderm.

In humans, the inner cell mass (ICM) of blastocyst generates human embryonic stem (hES) cells at the earliest stage of embryogenesis (J. A. Thomson et al., Science, 282, 1145 (1998)). The hES cells appear approximately 4-5 days post-fertilization with full self-renewal capacity and can yield all of the specialized cell phenotypes of the body. Human embryonic germ stem (hEG) cells, which are derived from fetal primordial germ ridge at 5-9 weeks post-fertilization, also possess pluripotency (M. J. Shambloff et al., Proc. Natl. Acad. Sci. USA, 95, 13726 (1998)). In vitro, both hES and hEG cells will spontaneously generate embryoid bodies (EBs) that consist of cell types from all three primary germ layers (M. Amit et al., Dev. Biol., 227, 271, (2000); M. J. Shambloott et al., Proc. Natl. Acad. Sci. USA., 98, 113, (2001)), giving an enormous potential to be used in cell-based therapies (K. Hochedlinger and R. Jaenisch, N. Engl. J. Med., 349, 275 (2003)).

Comparatively, research has paid less attention to the outer trophectoderm of blastocyst in humans. Most of the knowledge on hTS cells has been based on experiments on mice. In mice, trophectodermal subtypes initiate at peri-implantation to form three distinctive trophoblast cell layers. The trophectoderm overlying the ICM continue to divide and form the polar trophectoderm, which then grows into the extraembryonic ectoderm (ExE), where a diploid cell population is maintained with some develop into the mature chorioallantoic placenta (A. J. Copp, J. Embryol. Exp. Morphol., 51, 109 (1979)). This model presents ExE as a potential source of stem cells for the trophoblast lineage (J. Rossant and W. Tamura-L is, J. Embryol. Exp. Morphol., 62, 217 (1981)). In humans, research suggests that hTS cells may occur in the later stages of placental development rather than in the blastocyst (J. Rossant, Stem Cells 19, 477 (2001)). Another study suggests that no hTS cells exist, and that any possible existence of hTS cells would likely originate from the cytotrophoblast layer (T. Kunath et al., in: Trophoblast stem cells, chapter 12, in: Stem Cell Biology, D. R. Msrshak, R. L. Gardner, D. Gottlieb, Eds. (Cold Spring Harbor Laboratory Press, Cold Spring Harbor, N.Y. 2001), pp. 267-287).

Other possible disadvantages of the existing cell lines are as follows:

1. Use of feeder cells for culturing the human embryonic stem cell (hESC) lines produces mixed cell population that require the embryonic stem cells (ESC) to be separated from feeder cell components and this impairs scale up.

2. ESC get contaminated by transcripts from feeder cells and cannot be used on a commercial scale. It can be used only for research purposes.

U.S. Appl. No. 2003104616 disclosures that Geron established a procedure where hESC line was cultured in the absence of feeder cells (XU et. al 2001). The hESC were cultured on an extracellular matrix in a conditioned medium and expanded in this growth environment in an undifferentiated state. The hESC contained no xenogenic components of cancerous origin from other cells in the culture. Also, the production of hESC cells and their derivatives were more suited for commercial production. In this process, there was no need to produce feeder cells on an ongoing basis to support the culture, and the passaging of cells could be done mechanically. However, the main disadvantage of this procedure is that the inner cell mass (ICM) is isolated by immunosurgery method, wherein the initial derivation of ESC is carried out using feeder layer containing xenogenic components. This raises the issue of possible contamination with animal origin viruses and bacteria.

SUMMARY OF THE INVENTION

In one aspect, the present invention provides a method for isolating the ectopic pregnant mass-derived human villous trophoblast stem cell, comprising the steps of: (a) obtaining trophoblastic villi from a tubal ectopic pregnant mass; (b) collecting cells from the trophoblastic villi; and (c) culturing the collected cells in a culture medium to obtain the isolated human villous trophoblast stem cell. The subject method may further comprise cutting the trophoblastic villi into pieces and treating the trophoblastic villi with an enzyme.

In some embodiments, the ectopic pregnant mass-derived human villous trophoblast stem cell expresses embryonic stem cell antigens SSEA-1, SSEA-3 and SSEA-4. The ectopic pregnant mass-derived human villous trophoblast stem cell may also express genetic markers Octamer-4 (Oct 4), trophoblast-specific receptor (FGFR2), and fibroblast growth factor 4 (FGF4). In some embodiments, the ectopic pregnant mass-derived human villous trophoblast stem cell is capable of forming embryonic bodies with an adhesive characteristic. The ectopic pregnant mass-derived human villous trophoblast stem cell is also capable of maintaining the length of chromosomal telomeres in passages in culture. In some embodiments, the ectopic pregnant mass-derived human villous trophoblast stem cell is capable of differentiating into a mesenchymal cell expressing cell surface markers CD44 and CD90. In some embodiments, the ectopic pregnant mass-derived human villous trophoblast stem cell is capable of differentiating into an endodermal, mesodermal, and/or ectodermal cell. The ectopic pregnant mass-derived human villous trophoblast stem cell can be one selected from the group consisting of osteoblast, chondrocyte, myocyte, adipocyte, neural cell, pancreatic islet stem cell and progenitor cell. In some embodiments, the ectopic pregnant mass-derived human villous trophoblast stem cell has a gene-switching mechanism that is bFGF-dependent. A mutation can be introduced into the ectopic pregnant mass-derived human villous trophoblast stem cell so that the cell is genetically modified. In some embodiments, the ectopic pregnant mass-derived human villous trophoblast stem cell produces a growth factor or a hormone. One example of the hormone is human chorionic gonadotropin (hCG). In some embodiments, the pregnant mass is obtained in an unruptured manner. In some embodiments, the pregnant mass is at a gestational age of no older than 7 or 8 weeks. In some embodiments, the trophoblastic villi are obtained through a surgical procedure. In practicing the subject method, the culture medium can be free of a feeder layer. The method of the present invention can further comprise the steps of: (a) forming embryonic bodies (EBs) in the culture medium; (b) treating the EBs with an enzyme; and (c) collecting cells from the enzyme-treated EBs to obtain the isolated human villous trophoblast stem cell. Also provided by the present invention is an isolated human villous trophoblast stem cell prepared by the method described herein.

In another aspect, the present invention provides a method for treating or preventing a disease or a condition comprising administering to a subject in need thereof an effective amount of an isolated human villous trophoblast stem cell prepared using the subject method disclosed herein. In some embodiments, the disease is an immunodeficient disease, a nervous system disease, a hemopoietic disease, a cancer, or diabetes. The cancer can be a carcinoma. Examples of the cancer include an adenocarcinoma or choriocarcinoma. The choriocarcinoma can be syncytioma malignum. In some embodiments, the nervous system disease is a neurodegenerative disease. The neurodegenerative disease can be Parkinson's disease, Huntington's disease, Alzheimer's disease, amyotrophic lateral sclerosis (ALS), multiple system atrophy, Lewy body dementia, peripheral sensory neuropathy, spinal cord injury, or a chemical induced neuron damage. In some embodiments, the neurodegenerative disease is Parkinson's disease. The neurodegenerative disease may result in a loss or damage of dopaminergic neurons. In some embodiments, the human villous trophoblast stem cell differentiates into neuron in situ. In some embodiments, the human villous trophoblast stem cell differentiates into dopaminergic neuron in situ. In some embodiments, the human villous trophoblast stem cell, upon administration to the subject, migrates to substantia nigra pars compacta (SNc) region of the brain of the subject. In some embodiments, the condition is habitual abortion or implantation IVF failure. The subject method for treating or preventing a disease or a condition using the isolated human villous trophoblast stem cells may further comprise administering to the subject an effective amount of a therapeutic compound. The therapeutic compound can be a drug, a chemical, or an antibody. In some embodiments, the method further comprises administering to the subject an effective amount of a compound that modulates bFGF, Oct 4, FGFR-2 or FGF4. The compound can be an inhibitor of bFGF, Oct 4, FGFR-2 or FGF4. In some embodiments, the subject is a mammal, preferably a human. The administering of the cells can be via injection, transplantation, or surgical operation. In some embodiments, the administering of the human villous trophoblast stem cell is performed into the striatum region of the brain of the subject.

In yet another aspect, the present invention provides a method for screening for therapeutics that modulate human villous trophoblast stem cell differentiation or activity comprising: (a) subjecting an isolated human villous trophoblast stem cell prepared using the method of claim 1 to a test substance; and (b) evaluating the effect of the test substance to determine if the test substance modulates human villous trophoblast stem cell differentiation or activity.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 4 shows functional assessments of hTS cell-derived neural stem cells. a. Expression of F1B-FGP transfected hTS cells (green color). b. Expression of TH-2-FITC (green color) in induced neural stem cells. c. Expression of F1B-FGP in induced neural stem cells (green color). d. Expression of TH-16-PE (red color) in F1B-FGP transfected hTS cells. e. Co-expressions of TH-16-PE (red color) and F1B-FGP transfected (green color) in induced neural stem cells. A unilateral (right) 6-OHDA-lesion model of Parkinson's disease is performed in rats. Immunohistochemical assays after 6-OHDA-lesions showed no TH immunoreactivities were detected in the lesioned areas of striatum (str, upper, f), subthalamic nucleus (stn, lower, g), and substantia nigra compacta (snc, lower, not shown) in comparison with the positive responses (dark brown) in control areas. f. Treated with PBS as group c (gr. c). g. Treated with induced hTS cell-FGP transfected as group b (gr. b). h. Treated with non-induced hTS cell-FGP transfected as group a (gr. a) showed positive TH immunoreactivities in the previously lesioned striatum (upper, right) and substantia nigra compacta (lower, right). Immunofluoresent observation found several clusters of FGP-transfected hTS cells (green) scattered in the previously lesioned striatum (i) and a cluster of FGP-transfected hTS cells and some scattered cells (green) in the substantia nigra compacta (j). Arrow indicates needle tract. k. Apomorphine-induced rotation tests after 6-OHDA-lesioned hemiparkinsonian rats treated with induced and FGP-transfected hTS cells (gr. b, closed triangle) and treated with non-induced but FGP-transfected hTS cells (gr. a, closed circle). Control group was injected with PBS (gr. c). Significance (*: $p<0.05$) tested by LSD post hoc comparisons after repeated-measure ANOVA, $p=0.037$ (a vs. c) and $p=0.008$ (b vs. c) at 6 weeks; $p=0.019$ (a vs. c) at 9 weeks; $p=0.005$ (a vs. c) and $p=0.018$ (a vs. b) at 12 weeks.

FIG. 5 shows morphological differentiation and de-differentiation of hTS cells during drug induction into pancreatic islet-like cells. (a) Appearance in fibroblastic cells before induction. (b) Pre-induction with LDMEM-mn at 6 h with multicystic features and (c) after 24 h with grape-like cluster formation. (d) HDMEM-mn induction at 6 h with more apparent grape-like cell clusters. Fibroblastic outgrowths from the cell cluster appeared at 18 h (e), 48 h (f) and 96 h (g) after cultured in basic medium showing morphological de-differentiation. (h) Peak immunoreactive insulin secretion from differentiated hTS cells into culture medium appeared after HDMEM-mn induction for 6 h.

FIG. 7 shows immunocytochemistry of insulin-related proteins in differentiated hTS cells. Positive immunocytochemical reactions were detected in cells with (a) insulin, (b) insulin-like growth factor-1 (IGF-1), (c) glucagons, (d) amylase, (e) tau and (f) MAP-2.

FIG. 9 shows immunoreactive insulin in tissue derived from drug-induced hTS cells. Around 10 cell layers proliferated from both (a) non-drug-induced hTS cells as control and (b) drug-induced hTS cells as study by hematoxylin eosin stain. Negative immunoreactive insulin expression in control (c) but positive detection in study (d). Positive control of insulin staining is proformed in islet of normal pancreas (e) and cells of insulinoma (f).

DETAILED DESCRIPTION OF THE INVENTION

Term Definition

Figure 1A:
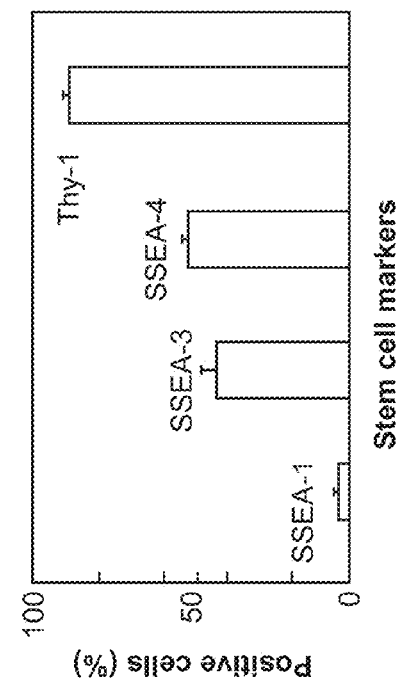
FIG. 1 shows display of hTS cells in early mesenchymal villi and term placenta. (a) tEBs formed from dispersed trophoblastic cells culture. (b) expressions of SSEAs and Thy-1 in the tEBs derived cells by flow cytometry. Immunocytochemically, SSEA-1 expressed in the cytoplasm (c) while SSEA-3 in the nucleus (d) and SSEA-4 in the cell membrane (e). Immunohistochemically, in the early cytotrophoblasts, SSEA-1 appeared mainly in the cell membrane and few in the cytoplasm (f), SSEA-3 in the nucleus (g), and SSEA-4 in the cell membrane (h). At term villi, detectable SSEA-1 (i), SSEA-3 (j), and SSEA-4 (k) shown in the mature intermediate villous stroma. SSEA-1 stained cells in the vein of fallopian tissue (l) and umbilical cord veins (m). SSEA-3 (n) and SSEA-4 (o) stained cells in the umbilical cord veins.

Gene therapy: the use of genes and the techniques of genetic engineering in the treatment of a genetic disorder or chronic disease. There are many techniques of gene therapy, all of them still in experimental stages. The two basic methods are called in vivo and ex vivo gene therapy. The in vivo method inserts genetically altered genes directly into the patient; the ex vivo method removes tissue from the patient, extracts the cells in question, and genetically alters them before returning them to the patient.

Immunodeficient disease: in medicine, immunodeficiency (or immune deficiency) is a state in which the immune system's ability to fight infectious disease is compromised or entirely absent. Most cases of immunodeficiency are either congenital or acquired.

Nervous system disease: refers to any condition characterized by the progressive loss of neurons, due to cell death, in the central nervous system of a subject.

Tumor: The tumor include abnormal cancer cells associated with lymphoma, leukemia, plasma cell dyscrasias, multiple myeloma, amylodosis, also as known as hematopoietic tumors, colorectal cancer, ovarian cancer, bone cancer, renal cancer, breast cancer, gastric cancer, pancreatic cancer, or melanoma.

This invention provides an isolated preparation of human trophoblast stem cells which is obtained from embryo at fallopian tube of ectopic pregnancy. The human trophoblast stem cell (hTS) is capable of indefinite proliferation in vitro in an undifferentiated state. The hTS cell maintains the potential multilineage differentiation capabilities. The hTS cell preparation can be induced to differentiate into cells of the trophoblast lineage in vitro or in vivo. The invention therefore also relates to a purified trophoblast stem cell preparation of the invention (preferably cultured in vitro) induced to differentiate into cells of the trophoblast lineage. This differentiated cell preparation is characterized by expression of genetic markers of trophoblast cell lineages (e.g. diploid trophoblast cells of the ectoplacental cone (EPC), and the secondary giant cells of the early conceptus). In an embodiment, the purified trophoblast cell isolation comprises cells of the trophoblast lineage including diploid trophoblast cells.

The isolated cells are positive for the SSEA-1 marker, positive for the SSEA-3 marker, and positive for the SSEA-4 marker, are pluripotent and have karyotypes and in which none of the chromosome are altered. In an embodiment, the cells are characterized by expression of the genetic markers Oct 4, fgfr-2, and FGF4.

The isolated hTS cell has normal karyotypes after subsequent cultures in vitro, which maintains length of telomere which does not become shorter after subsequent cultures in vitro.

In the preferred embodiment, the hTS cells are positive for cell surface markers CD44 and CD90. Further, the hTS cells can be induced for differentiating into several kinds of cells. In the preferred embodiment, the cells differentiate into endodermal, mesodermal, and/or ectodermal derivatives. In more preferred embodiment, the derivative is osteoblast, chondrocyte, myocyte, adipocyte, and/or neural stem cell. For differentiating into different functional cell types, the cells have gene switch. In the preferred embodiment, the gene switch is induced by bFGF.

The hTS is provided for use in model of human cell differentiation, gene therapy, or cell-based therapy.

The isolated hTS cell can be modified by introducing mutations into genes in the cells or by introducing transgenes into the cells. Insertion or deletion mutations may be introduced in a cell using standard techniques. A transgene may be introduced into cells via conventional techniques such as calcium phosphate or calcium chloride co-precipitation, DEAE-dextran-mediated transfection, lipofection, electroporation, or microinjection. Suitable methods for transforming and transfecting cells can be found in Sambrook et al. (Molecular Cloning: A Laboratory Manual, 2nd Edition, Cold Spring Harbor Laboratory press (1989)), and other laboratory textbooks. By way of example, a transgene may be introduced into cells using an appropriate expression vector including but not limited to cosmids, plasmids, or modified viruses (e.g. replication defective retroviruses, adenoviruses and adeno-associated viruses). Transfection is easily and efficiently obtained using standard methods including culturing the cells on a monolayer of virus-producing cells.

The hTS cell preparations of the invention can be used to produce growth factors, hormones, etc. relevant to human placenta. The cell preparations or cell lines of the invention can also be used to produce therapeutics such as human Chorionic Gonadotropin (hCG).

The hTS cell preparations of the invention can be used to screen for genes expressed in or essential for trophoblast differentiation. Screening methods that can be used include Representational Difference Analysis (RDA) or gene trapping with for example SA-lacZ. Gene trapping can be used to induce dominant mutations (e.g. by deleting particular domains of the gene product) that affect differentiation or activity of trophoblast cells and allow the identification of genes expressed in or essential for trophoblast differentiation.

This invention also provides a method for obtaining human stem cells comprising (a) obtaining embryo at fallopian tube of ectopic pregnancy; and (b) obtaining the stem cells from the villous trophoblast of the embryo; wherein the human stem cells are human trophoblast stem cells as described above. The embryo is obtained from the unruptured ectopic pregnancy. In a preferred embodiment, the unruptured ectopic pregnancy is in the stage less than 6 weeks postfertilization. The villous trophoblast comprises cytotrophoblastic layer.

This invention also provides a combination for therapy comprising (a) an isolated preparation of human trophoblast stem cells and (b) a buffer solution, wherein the human stem cells are human trophoblast stem cells as described above. The buffer solution of the combination is provided for maintaining biological activities of the stem cells. For example but not limiting, the buffer solution is saline, PBS, and medium.

The combination further comprises a therapeutic compound. For example but not limiting, the therapeutic compound is drug, chemical, and antibody. In an embodiment, the therapeutic compound is immunosuppressive agent or supportive agents.

The combination of this invention is provided for therapy of diseases comprising immunodeficient diseases, nervous system diseases, hemopoietic system diseases, or tumors. The combination of this invention is used in transplantation, injection, or external application.

This invention further provides a method for monitoring the status of contraception comprising assaying bFGF, Oct4, fgfr-2, and/or FGF4 levels in the endometrium, wherein the status of contraception is directed to implantation and placentation.

This invention further provides a composition for use in the treatment of patients suffering from habitual abortion and/or IVF failure comprising monocloned antibodies, antagonists and other inhibitors to regulate bFGF, Oct4, fgfr-2, and FGF4 levels, wherein the treatment involves Oct4 and fgfr-2 expressions knockdown by bFGF. The IVF failure is frequent IVF failure.

This invention further provides a method for use in treating or preventing cancer comprising administering to an animal in need thereof an effective amount of monocloned antibodies, antagonists and other inhibitors to regulate bFGF, Oct4, fgfr-2, and FGF4 levels. In an embodiment, the animal is mammalian. In a preferred embodiment, the animal is human.

The method of this invention can be used in treating or preventing cancer, wherein the cancer is carcinoma. Further, the carcinoma is adenocarcinoma or choriocarcinoma. In a preferred embodiment, the choriocarcinoma is syncytioma malignum.

This invention further provides a composition for treating a nervous system disease comprising human trophoblast stem cells, wherein the human trophoblast stem cells are obtained from embryo of ectopic pregnancy. The nervous system disease is neurodegenerative disease. Neurodegenerative disease refers to any condition characterized by the progressive loss of neurons, due to cell death, in the central nervous system of a subject. In the preferred embodiment, the neurodegenerative disease is Parkinson's disease, Huntington's disease, Alzheimer's disease, amyotrophic lateral sclerosis (ALS), multiple system atrophy, Lewy body dementia, peripheral sensory neuropathies or spinal cord injuries. In the more preferred embodiment, the disease neurodegenerative disease is Parkinson's disease.

The composition of this invention further comprises a buffer solution, which is provided to maintain the bioactivities of the human trophoblast stem cell. For example but not limiting, the buffer solution is saline, PBS, and medium.

The composition of this invention further comprises a therapeutic compound. For example but not limiting, the therapeutic compound is drug, chemical, and antibody.

This invention further provides a method for treating a neurodegenerative disease comprising administering a patient with an effective amount of trophoblast stem cells. The trophoblast stem cell is obtained from trophoblastic villi at fallopian tube of ectopic pregnancy. In the preferred embodiment, the neurodegenerative disease is Parkinson's disease, Huntington's disease, Alzheimer's disease or chemical-induced neuron damage.

The administering is via injection, transplantation or surgical operation.

In the embodiment, the patient is animal. In the preferred embodiment, the animal is human.

This invention also provides a composition for treating diabetes comprising human trophoblast stem cell as described above. The composition further comprises a pharmaceutical acceptable carrier, wherein the carrier is for maintaining bioactivities of the stem cell. For example but not limiting, the carrier is saline, PBS, and medium.

The composition of this invention can be administered by injection, transplantation or surgical operation. The concentration or amount of the composition can be well judged by the person skilled in the art.

EXAMPLE

The examples below are non-limiting and are merely representative of various aspects and features of the present invention.

Example 1

Primary Culture and Isolation of hTS Cells from Trophoblastic Villi

Figure 10A:
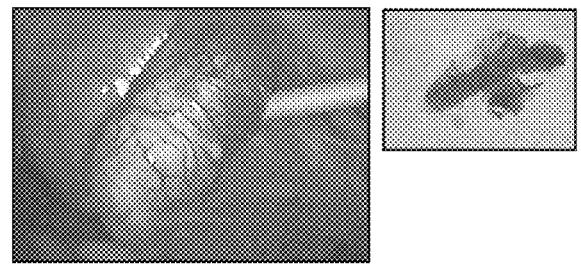
FIG. 10 shows ectopic tubal pregnancy mass at 4-5 weeks post fertilization laparoscopically (a, left) and the trophoblastic villi are dissected for further preparation and establishment of cell line (a, right). (b) and (c) shows immunohistochemical examinations of SSEAs expression on trophoblastic villi and fallopian tissues. (b) SSEA-1 expressed cells are seen in the loose stromal mesoderm (black arrow head), capillary wall (white arrow), and capillary intralumen (white arrow head). SSEA-3 and SSEA-4 were negative staining. (c) SSEA-1 expressed cells appeared in a vessel of fallopian tissue.

Using a laparoscopy, eight eligible samples (4-5 weeks post-fertilization) were obtained from the gynecologic unit (FIG. 10a). The samples were used for cell culture and for immunohistochemical study. Fresh villi (FIG. 10b) were mechanically dissected, washed, and cultured with medium in the absence of bFGF. Prior to differentiation, only few EBs appeared on day one of the culture (FIG. 1a). After a week, EBs count increased to 30-40 in number with identical morphological features described in previous studies (M. Amit et al., Dev. Biol., 227, 271, (2000); M. J. Shambloott et al., Proc. Natl. Acad. Sci. USA., 98, 113, (2001)).

Figure 10B:
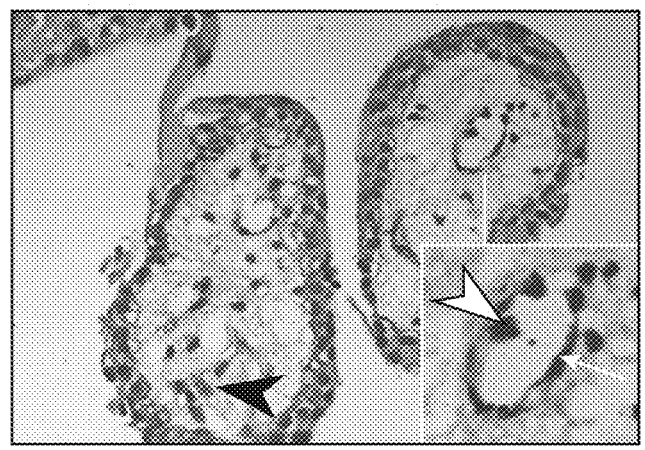

Early trophoblastic villi were obtained from the unruptured tubal ectopic pregnant mass 4-5 weeks post fertilization (FIG. 10a) under laparoscopic surgery. Immediately, villous tissues were washed by normal saline (37° C.) to get rid of blood and dissected in serum free α-MEM medium (minimum essential medium modification α-MEM, Sigma-Aldrich, St. Louis, Mo.) microscopically to avoid contamination with embryonic compartment. Villi were cut into very small pieces and transferred to a 15 ml conical tube for 3 min at room temperature (FIGS. 10b and c). The supernatant was removed for centrifugation at 1500 rpm for 6 min. After centrifugation, the pellets were digested with 0.025% trypsin/EDTA (Sigma-Aldrich) in final dilution at 37° C. for 40 min. Digestion was stopped by adding .alpha.-MEM containing 10% fetal bovine serum and washed again. The pellets were re-suspended with 8 ml α-MEM containing 20% FBS (HyClone, Logan, Utah) and 1% penicillin/streptomycin, seeded onto two 10 cm culture dishes and incubated in 5% $CO_2$ at 37° C.

Embryonic bodies (EBs) formed after day 2 of culture. The EBs might increase to 30-40 in number after one week of culture. These EBs were collected, trypsinized as before and cultured again. By 7-10 days, a monolayer of fibroblast-like cells formed. They were trypsinized and washed twice by PBS. The cells were collected for storage in liquid nitrogen by adding 10% DMSO/FBS (Sigma-Aldrich).

In the culture, the EBs appeared to adhere to the dish, as opposed to those derived from hEG cells, which tend to float in a suspended state (B. Gerami-Naini et al., Endocrinology, 145, 1517 (2004); L. Cheng, H. Hammond, Z. Ye, X. Zhan, G. Dravid, Stem Cells, 21, 131 (2003)). What caused this difference remains unclear. We suggest that the adhesiveness might be related to the implantation characteristics of trophoblast. The EBs were then trypsinized and cultured again. The harvested cells were either moved immediately to the study or stored with liquid nitrogen and later thawed before use.

For cell culture, the cells were thawed and re-cultured in conditioned α-MEM medium containing 20% FBS, 1% penicillin-streptomycin and with 10 ng/ml bFGF (CytoLab Ltd, Rehovot, Israel) or without bFGF at 37° C. with 5% $CO_2$. Medium was changed after 3 days of culture. Half the medium was changed every 3 days thereafter. Cells were passaged by trypsinization upon reaching 90-95% confluence of the dish. After 5 passages, differentiations into a variety of specific cell phenotypes were performed to ensure the capability for multilineage pluripotency. hCG in culture medium were determined by a specific radioimmunoassay kit (Diagnostic Products, Los Angeles, Calif.).

Example 2

Immunocytochemical Study of Differentiated hTS Cells

At passage 6, cells were cultured as a monolayer in basal medium (α-MEM containing 20% FBS and 10 ng/ml bFGF) in 3.5 cm culture dishes. After cells grew to 70% in confluence, culture medium was changed for variable differentiations. The evaluations were made at day 7, 14, 21, and 28 after drug induction. For osteogenic differentiation, cells were grown in conditioned medium (Table 1).

Table 1 Recipes Used for Specific Cell Phenotype Differentiations of hTS Cells

TABLE 1

Recipes used for specific cell phenotype differentiations of hTS cells

| Differentiations | Reagents |
| --- | --- |
| Osteogenesis | α-MEM containing 20% FBS, 10 μg/ml bFGF, 0.1 μM dexamethasone, 10 mM β-glycerolphosphate, and 0.2 mM ascorbic acid |
| Chondrogenesis | α-MEM containing 10% FBS, 1% antibiotic/antimycotic, 6.25 μg/ml insulin, 10 ng/ml TGF-β1, and 50 nM ascorbate-2-phosphate |
| Myogenesis | α-MEM containing 10% FBS, 10 μg/ml bFGF, 0.1 mM dexamethasone, 50 mM hydrocortisone, and 5% horse serum |
| Adipogenesis | α-MEM containing 20% FBS, 10 μg/ml bFGF, 10 μg/ml insulin, 1 μM dexamethasone, 0.5 mM isobutyl methylxanthine, and 200 μm indomethacin. |
| Neurogenesis | α-MEM containing 20% FBS and 10 μM all trans-retinoic acid |
| Pancreaticislet beta-cells | L-DMEM containing 20% FBS, 5.5 mmol/L glucose, 10 mmol/L nicotinamide, 1 mmol/L β-mercaptoethanol, H-DMEM containing 15 mmol/L glucose, 10 mmol/L nicotinamide, 1 mmol/L β-mercaptoethanol |
| HBS solution | NaCl: 867 g in 80 ml Milli Q, 2 ml 1 M HEPES (GIBCO HEPES Buffer solution cat. No.: 15630-080), adjusted pH to 7.4 and filted by 0.2 μm filter and stored at 4° C. |

Medium changes were performed twice weekly, with a medium volume of 2 ml per dish. The cells were subjected to immunocytochemical stains. (A) Cytochemical mineral matrix was analyzed by Alizarin red S (AR-S) assay to identify its calcium mineral content (S1). Cells were rinsed with PBS followed by fixation in ice-cold 70% ethanol for 1 h and rinsed with de-ionized water followed by 40 mM AR-S (pH 4) at room temperature for 10 min. The cells were then rinsed five times with water and then washed with PBS for 15 min to reduce non-specific AR-S stain. (B) For von Kossa stain (S2), cell layers were fixed with 10% formaldehyde for 1 h, incubated with a 2% silver nitrate solution (w/v) for 10 min in the dark, washed thoroughly with de-ionized water, and then exposed to bright light for 15 min. (C) Alkaline phosphatase activity was measured using a commercial kit (Sigma-Aldrich) (S3). (D) Chondrogenic differentiation (S4) was induced with a conditioned medium (Table 1). Chondrogenesis was confirmed by Alcian blue (Sigma-Aldrich) staining at an acidic pH. Cells were fixed with 4% formaldehyde for 15 min at room temperature and washed with PBS several times, then incubated for 30 min with 1% Alcian blue in 0.1 N HCl (pH 1.0) and finally, washed with 0.1 N HCl for 5 min to remove excess stain. (E) Myogenic differentiation (S4) was induced in conditioned medium (Table 1) for 4 weeks and confirmed by immunocytochemical staining for the myosin heavy chain. Cells were rinsed twice with PBS, fixed for 20 min with 4% formaldehyde, and washed several times with PBS. The cells were then incubated with 3% hydrogen peroxide in PBS for 10 min to quench endogenous peroxidase enzyme activity, and non-specific sites were blocked by incubation in blocking buffer (PBS containing 10% HS, 0.1% Triton X-100) for an additional 60 min. The cells were washed three times for 5 min each in blocking buffer and incubated for 1 h in blocking buffer containing skeletal muscle myosin heavy chain specific monoclonal antibody (Vector Laboratories). The cells were washed in blocking buffer and detected using the VectaStain ABC kit (Vector Laboratories). (F) Adipogenic differentiation (S5) was induced in conditioned medium (Table 1). Cells were fixed for 60 min at room temperature in 4% formaldehyde/1% calcium and washed with 70% ethanol. They were incubated in 2% oil red O reagent for 5 min at room temperature. Excess stain was removed by washing with 70% ethanol followed by several changes of distilled water. The assay was using an oil red O stain as an indicator of intracellular lipid accumulation.

Immunohistochemically, detection of the SSEA-1 (Chemicon, D3P013A), SSEA-3 (Chemicon, 24040550), and SSEA-4 (Chemicon, 24080406) expressions was performed using LSAB kit (Dako, k0697) and Double AB (Dako, k3466). Goat serum (Dako, x0907) was used as a blocking antigen. The staining procedures of SSEA-1 and SSEA-4 on the de-paraffined tissue sections were as follows: 1) rinsing with tris-phosphate buffer saline (TBS); 2) cleaning by $H_2O_2$ for 10 min; 3) blocking with goat serum for 30 min; 4) adding primary antibody and incubated for overnight; 5) rinsing with TBS; 6) treated with streptavidin for 20 min; 6) rinsing with TBS; 7) stained by biotin (20 min); 8) washing with TBS 9) treated with DAB (10 min) and counterstained with Mayer hematoxylin. For SSEA-3 staining, similar procedures were done. An additional step: retrieve antigen by high pressure cooker in citrate buffer for 15 min, was added between step 1 and 2. As a result, expressions of SSEA-1, SSEA-3, and SSEA-4 appeared in the intracytoplasm, the nuclear membrane, and the cell membrane, respectively. However, a small number of cultured cells showed SSEA-4 staining in both intracytoplasm and cell membrane.

Figure 1B:
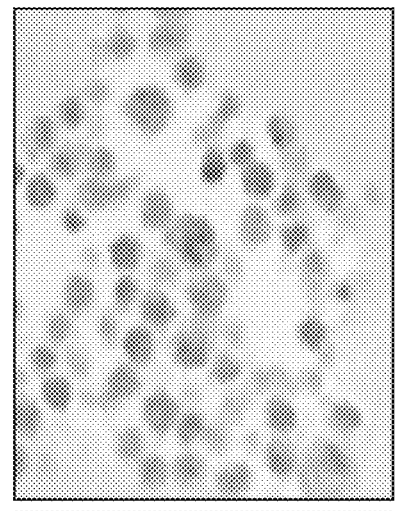
Figure 1C:
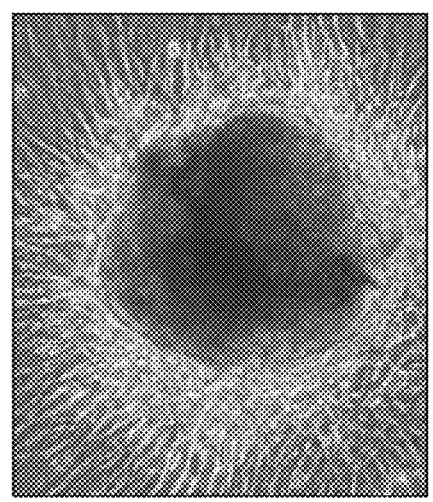
Figure 1D:
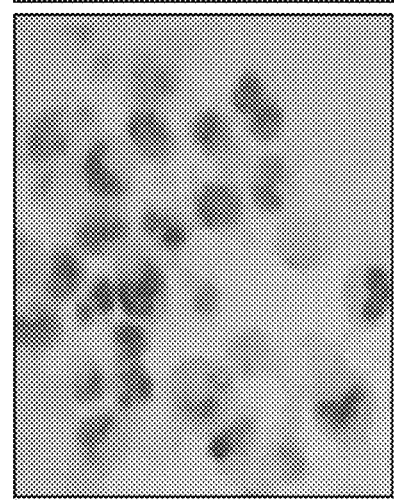
Figure 1E:
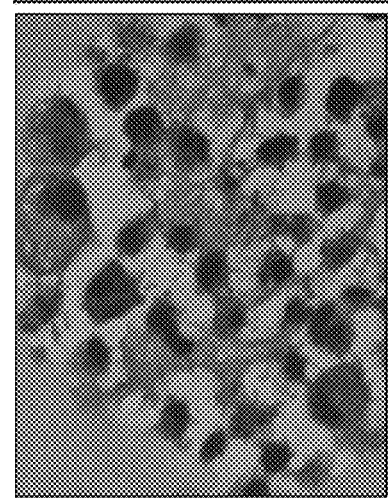

First, essential surface markers were applied to detect the existence of stem cells in the culture. After the first passage, cells were fixed in neutralized 4% formaldehyde and subjected to immunocytochemical tests for the essential surface markers of stem cell; stage-specific embryonic antigens, SSEA-1, SSEA-3, and SSEA-4. The results positively indicated the existence of pluripotent stem cells. Some giant cells displayed SSEA-1 in the cytoplasm of cells (FIG. 1c). SSEA-3 appeared in the nuclear membrane (FIG. 1d), while SSEA-4 appeared in both the cytoplasm and cell membrane (FIG. 1e). The cell was large and round in shape with a 1:1 nucleus to cytoplasm ratio.

Figure 10C:
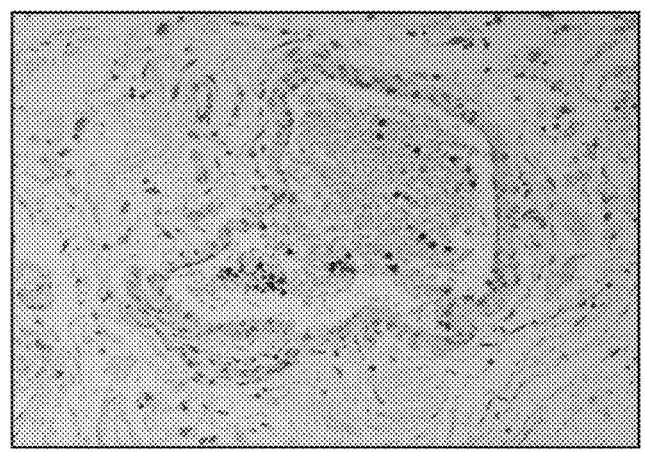

The SSEA expressions immunohistochemically were further confirmed by examining the locations of these SSEAs in the ectopic villous tissues. In the villi, all SSEA stained cells were localized at the Langhans layer (inner layer), where SSEA-1 expressions appeared in the cytoplasm of cells (FIG. 1f). SSEA-1 stained cells were also found in the loose mesodermal stroma, the endothelium of capillary, and the intraluminal space (FIG. 10b). SSEA-1 stained cells could also be seen in the lumen of vessels of the fallopian tissues (FIG. 10c). SSEA-3 and SSEA-4 appeared in the nuclear membrane and cell membrane, respectively (FIGS. 1g and h) (Table 1).

With SSEA expressions in the Langhans layer, it was proceed with immunostaining of human chorionic gonadotropins (hCG), an indication of the existence of trophoblastic cells. This invention resulted with hCG expression only in the syncytiotrophoblasts (outer layer) but not in the Langhans layer. The lack of hCG expression in the Langhans layer suggests that hTS cells are distinct from syncytiotrophoblast cells. To further support these findings, it was measured SSEA-1, SSEA-3, SSEA-4, and Thy-1 expressions using various antibodies by flow cytometry. In three cell lines (PV 02, PV 06, and PV 07), the cells that expressed with SSEA-1, SSEA-3, SSEA-4, and Thy-1 occupied 6.8±1.5%, 43.2±4.9%, 53.2±0.8%, and 94.3±1.8% of 10,000 cell counts, respectively (FIG. 1b). It was observed that SSEA-4 expression appeared in both the cytoplasm and the cell membrane immunocytochemically, but it appeared only in the cell membrane immunohistochemically. This result possibly reflects the different developmental status of the cytoplasm and the cell membrane of the cells.

In term placentae, cells stained with SSEAs were not found in the terminal villi, but in the intravillous stroma of larger stem villi (FIGS. 1i, j). SSEA-3 was distributed in the syncytial sprouts as well (FIG. 1k). Together, these findings provide evidence that in the early mesenchymal villi, hTS cells are located at a histological site identical to that of cytotrophoblasts and express all SSEAs surface markers.

Figure 1O:
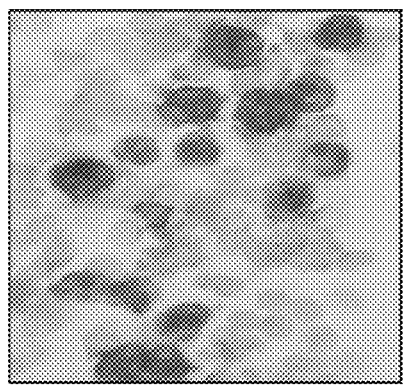
Figure 1N:
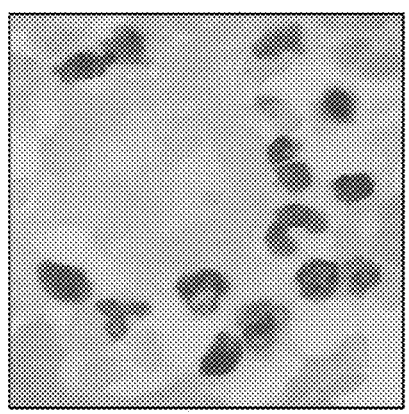
Figure 1M:
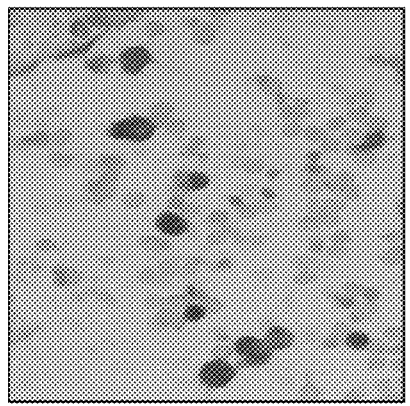
Figure 1L:
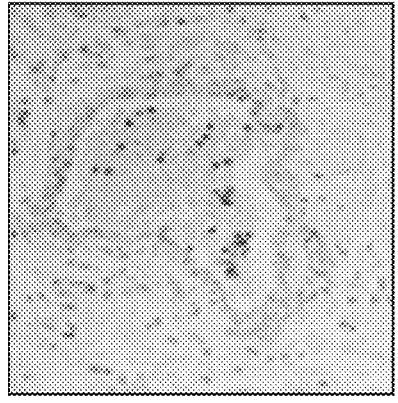

Because SSEA-1 stained cells were observed in the venous vessels of the tubal tissues in ectopic gestation (FIG. 11), the relationship between umbilical cord blood-derived mesenchymal stem cells and the hTS cells had to be clarified. To do this, it was investigated whether the SSEAs-stained cells appeared in blood vessels of term placentae located near the placenta-umbilical cord junction. An abundance of SSEA-1- (FIG. 1m), SSEA-3-(FIG. 1n), and SSEA-4-stained cells (FIG. 1o) were observed in the umbilical veins, but not in the artery.

These results prompted to ask whether those cells possess pluripotent capability in differentiation into a variety of specific cell phenotypes as hES/hEG cells do. The cells were cultured in different conditioned α-MEM media according to the differentiation induction. hCG was measured using radioimmunoassay and became undetectable after passage 1 (PV 07 cell line) and passage 2 (PV $O_2$ cell line) in the culture medium. After 6 passages, differentiations of specific cell phenotypes including osteoblasts, chondrocytes, adipocytes, myocytes, and neural cells were initiated by a variety of drug inductions (Table 1). Immunocytochemical evaluations were made on day 7, 14, 21, and 28 after induction (12).

The results demonstrated positive stains with Alizarin red S, von Kossa, and alkaline phosphatase for osteoblasts (FIGS. 2b, c and d), Alician blue for chondrocytes (FIG. 2e), myosin heavy chain for myocytes (FIG. 2f), and oil red O and intracellular lipid formation for adipocytes (FIG. 2g). This illustrated that the cells possess mesenchymal pluripotency for differentiation to specialized cell phenotypes, depending on the drugs administered.

Example 3

RT-PCR

Extraction of total RNA from the hTS cells (105 to 106) at various passages of culture and term placental tissues was carried out using the TRIzol kit according to the manufacturer's instructions (Invitrogen, Carlsbad, Calif.). Reverse transcription was performed using 1 μg RT reactions were performed using Ready-to-Go, RT-PCR Beads kit (Amersham Biosciences, Buckinghamshire, UK). One .mu.g of total RNA was reverse transcribed to cDNA. The cDNA product, corresponding to 0.2 μg of total RNA, was used for PCR amplification. The primers used were shown in Table 2.

Table 2 Primer Sequences Used for RT-PCR

SEQ ID NOS 1-26, Respectively, in Order of Appearance)

TABLE 2

| Primer sequences used for RT-PCR | |
|---|---|
| Osteopontin | (5'-CTAGGCATCACCTGTGCCATACC-3' forward and 5'-CAGTGACCAGTTCATCAGATTCATC-3' reverse) |
| Osteocalcin | (5'-CGCAGCCACCGACACACCAT-3' forward and 5'-GGGCAAGGGCAAGGGGAAGA-3' reverse) |

TABLE 2-continued

Primer sequences used for RT-PCR

| | |
|---|---|
| Perlecan (PRLN) | (5'-CATAGAGACCGTCACAGCAAG-3' forward and 5'-ATGAACACCACACTGACAACC-3' reverse) |
| Collagen typeII | (5'-ACGGCGAGAAGGGAGAAGTTG-3' forward and 5'-GGGGGTCCAGGGTTGCCATTG-3' reverse) |
| Myogenin | (5'-AGCGCCCCCTCGTGTATG-3' forward A and 5'-TGTCCCCGGCAACTTCAGC-3' reverse) |
| MyoD1 | (5'-CGGCGGCGGAACTGCTACGAA-3' forward and 5'-GGGGCGGGGCGGAAACTT-3' reverse) |
| PPARγ-2 | (5'-GCTGTTATGGGTGAAACTCTG-3' forward and 5'-ATAAGGTGGAGATGCAGGCTC-3' reverse) |
| Adipsin | (5'-GGTCACCCAAGCAACAAAGT-3' forward and 5'-CCTCCTGCGTTCAAGTCATC-3' reverse) |
| Pdx-1 | (5'-GTCCTGGAGGAGCCCAAC-3' forward and 5'-GCAGTCCTGCTCAGGCTC-3' reverse) |
| Oct4 | (5'-GGAAAGGCTTCCCCCTCAGGGAAAGG-3' forward and 5'-AAGAACATGTGTAAGCTGCGGCCC-3' reverse) |
| fgfr-2 | (5'-GGAGGGGATGTGGAGTTTGT-3' forward and 5'-ACTGGTTGGCGTGCCCTATA-3' reverse) |
| FGF4 | (5'-AGCGAGGCGTGGTGAGCATCTT-3' forward and 5'-TGGTCCGCCCGTTCTTACTGAG-3' reverse) |
| β2-microglobulin | (5'-CTCGCGCTACTCTCTCTCTTTCTGG-3' forward and 5'-GCTTACATGTCTCGATCCCACTTAA-3' reverse) |

Primer used for the reaction products were applied with electrophoresis in a 1.5% agarose gel and visualized with ethidium bromide. Primer for p2-microglobulin was used as cDNA positive control to assure even loading of the gel. For each set of PCR reaction, a control, in which water was added rather than cDNA, was included. Each control reaction was uniformly negative.

Figures 2H, 2I:
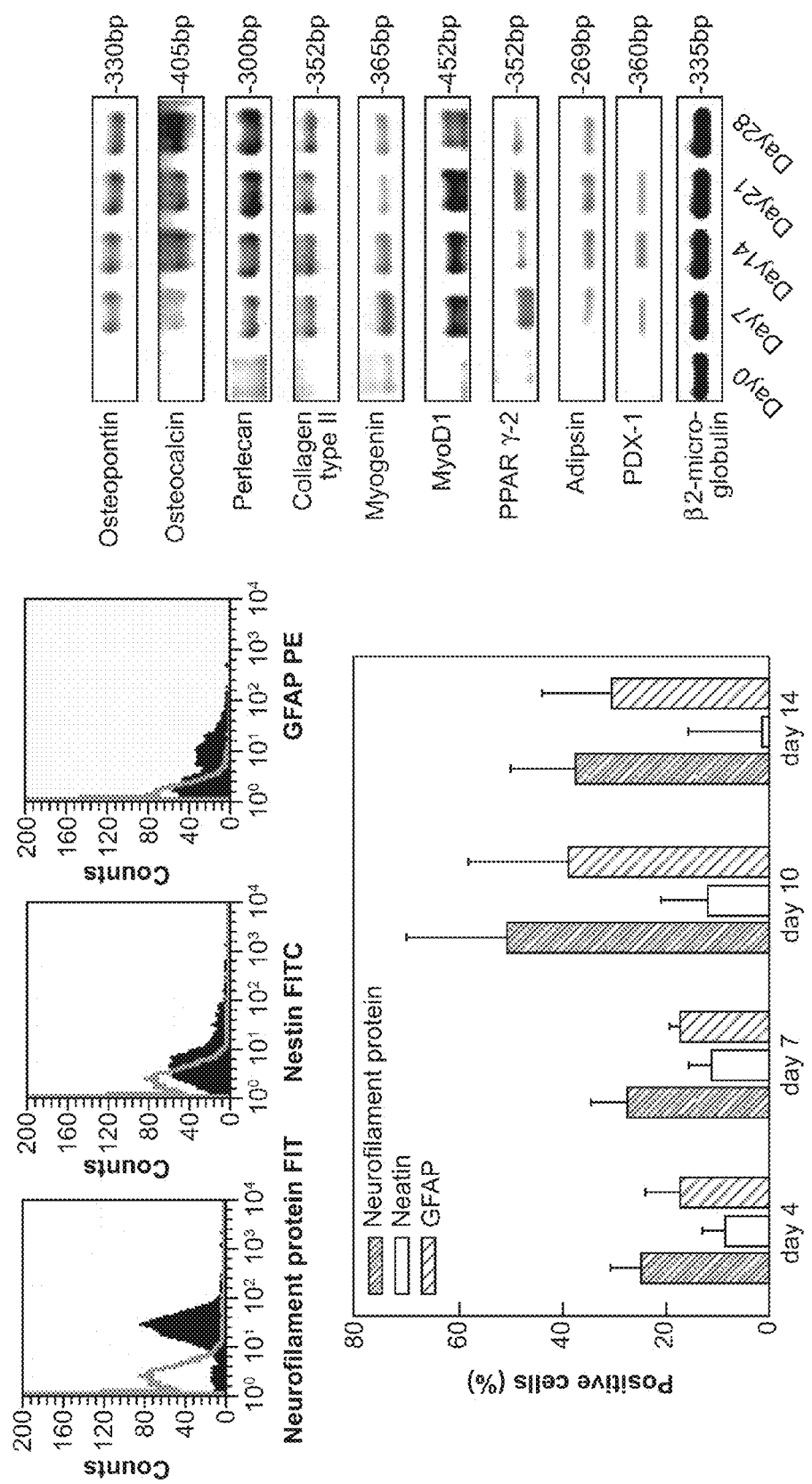
FIG. 2 shows in vitro differentiations of hTS cells into specific cell phenotypes of all three germ layers. (a) tEBs derived mesenchymal stem cells by flow cytometry. CD 44 and CD 90 for mesenchymal stem cells (upper), CD 34 and CD 45 for hematopoietic stem cells (lower). Osteogenic differentiation identified with: Alizarin red S (b), von Kossa (c), and alkaline phosphatase activity stains (d); Alician blue for chondrogenesis (e); Myosin heavy chain stain for skeletal muscle (f); and Oil red O for adipogenesis (g). (h) Neural stem cells: neurofilament (left), nestin (middle), and GFAP (right) measured by flow cytometry (upper). The peak responsiveness for neurofilament and GFAP was at 10th day of induction, while that of nestin was less (lower). (i) Gene expressions by RT-PCR analyses: osteopontin and osteocalcin for osteoblasts; perlecan and collagen type II for chondrocytes; myogenin and myoD1 for myocytes; PPAR.gamma.-2 and adipsin for adipocytes; and PDX-1 for pancreatic islet beta-cells. Positive expressions appeared 7 days after induction.

With RT-PCR, various primer sequences were used to identify the genetic expressions in the cultured cells (PV 02, passage 4). The primers used included: osteopontin and osteocalcin for osteoblasts, perlecan and collagen type II for chondrocytes, myogenin and myoD1 for myocytes, PPAR-.gamma.-2 and adipsin for adipocytes (12) (Table 2). The results indicated that all the above genetic expressions appeared within 7 days after induction in the cells (FIG. 2i). Among them, very strong gene expression was seen in myoD1 at 7 days. Additionally, neurogenic differentiation of the cells (PV 02 at passage 5, PV 07 at passages 3 and 4) was induced by retinoic acid and detected by flow cytometry. Expressions of neurofilament protein, GFAP, and nestin could be detected at day 4 after induction. Expressions of neurofilament protein (the strongest) and GFAP upregulated to day 10 then diminished. Very weak expression of nestin was seen in the first 10 days and disappeared after 14 days of induction (FIG. 2h). These results confirmed that in an undifferentiated state, these cells possess capability for differentiation to mesenchymal multilineages similar to that of hES/hEG cells.

Example 4

Chromosome and Telomere Length Analyses hTS cells were incubated with 0.1 μg/ml of colcemid for 3 hours. After trypsinization, they were re-suspended in 0.075 mol/L of KCl, incubated for 20 minutes at 37° C., and then fixed in methanol/acetic acid at a ratio of 3:1. Metaphase chromosomes were obtained from a 25 cm culture flask of hTS, according to standard procedures, and analyzed after G-banding (S7). Karyotype of human chromosomes was examined after staining by cytogenetic specialists.

Since the presence of telomerase activity does not always imply that telomere length will be stable and static. Telomerase activity is upregulated when stem cells are stimulated to generate progenitor cells (S8). We selected to measure the telomere length to see whether the telomere shortening occurred in hTS cells during subsequent culture (S9). Thus, genomic DNA was prepared in a 10 cm cell culture dish, grown to saturation, and digested with Hinf I and Rsa I before electrophoresis on a 1% agarose gel. The fragments were transferred to Hybond N+nylon membranes (Amersham) and hybridized at 65 degrees to a probe (TTAGGG repeats) labeled with $\alpha$-$^{32}$P-dCTP using Ready-To-Go labeling beads (Amersham Biosciences, UK). Telomere length was assessed by Southern blot analysis of terminal restriction fragments (TRFs) obtained by digestion of genomic DNA. The TRFs obtained contain DNA with uniform telomeric (TTAGGG) repeats as well as degenerated repeats other than at the distal end of the chromosome sub-telomeric region. After digestion, the DNA fragments are separated by gel electrophoresis and blotted. TRFs were visualized by hybridization with labeled oligonucleotides complementary to the telomeric repeat sequence. Finally, the size distribution of the TRFs can be compared to a DNA length standard. The results indicated that hTS cells at passage 3 and 7 (PV $O_2$ cell line) showed 8.0 kb and 7.8 kb, respectively. It has been reported that telomere length might be decreased with the number of cell divisions in vitro and with aging in vivo (S10, S11). Although no significant loss of telomere length was seen in the present observation, we can not exclude the possibility that the decrease of 200 bp by 4 passages in the culture was caused by the pre-existing variability in telomere length or by cell-to-cell variation of the rates of telomere shortening. This needs further elucidation.

Figure 3A:
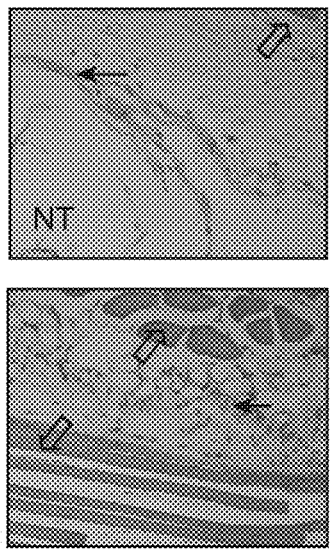
FIG. 3 shows in vivo characteristics and functionality of hTS cells. (a) hTS cell-induced chimeric reactions in SCID mice; (upper) needle tract (NT) and (lower) bizarre cells (black arrow) between the muscle fibers (blank arrow). (b) Karyotype of the hTS cells with 46 normal chromosomes (XY). (c) Telomere length of hTS cells at passage 3 (8.0 kb) and passage 7 (7.8 kb). (d) Functionality of hTS cells analyzed by RT-PCR. In lane 1, primary cultured hTS cells expressed Oct4, fgfr-2, and FGF4, and in lane 2 Oct4 and fgfr-2 were down regulated by adding bFGF (10 ng/ml) in hTS cells (passage 6). In lane 3 no bFGF was to hTS cells (passage 6). In lane 4 only fgfr-2 was expressed in the term placental cells. p2-microglobulin as cDNA positive control.
Figure 3B:
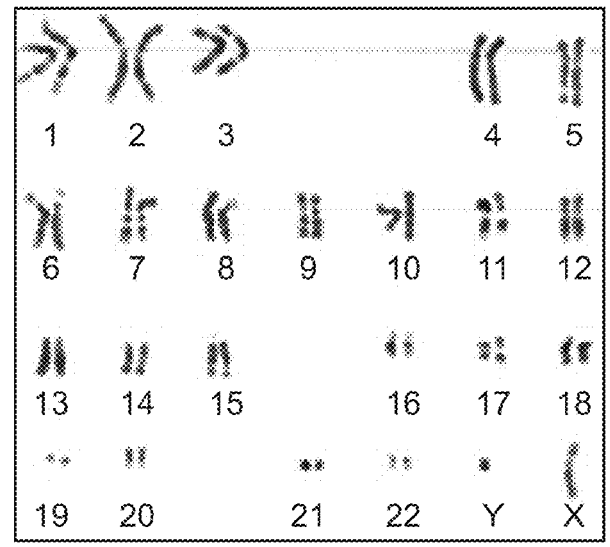
Figure 3C:
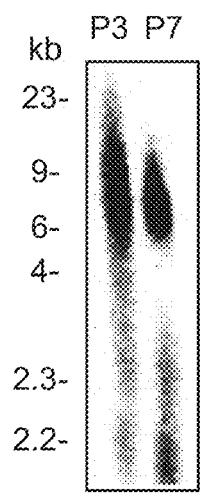

The capability of those cells in producing benign teratoma was examined as hES cells do in vivo. Cultured cells ($10^4$-$10^5$) at passage 3 of PV 02 cell line were prepared and injected subcutaneously into severe combined immunodeficient mice (n=4) at the rear thigh. Histopathologically, myxoid cell-like chimeric reactions formed after 8 to 10 weeks of injection (FIG. 3a), suggesting similar characteristics to hES cells during embryogenesis. Meanwhile, the chromosomes of these cells (46XY) at passages 3, 10 and 15 (PV 02 cell line) were analyzed, displaying normal and identical karyotypes (12) (FIG. 3b). Moreover, telomere lengths were measured in the cultured cells (PV 02) at passages 3 and 7 with a result of 8.0 kb and 7.8 kb, respectively (12). Since the chromosome had not become shorter, this indicates that no genetic information was lost in these cells during the subsequent cultures (FIG. 3c). Given these observations in karyotypes and telomere lengths, it was believed that hTS cells are present in the early trophoblastic villi and display the same characteristics as hES/hEG cells. It was suggested that hTS cells may be a progenitor of human umbilical cord blood stem cells. Furthermore, both cord blood-derived mesenchymal stem cells and hTS cells contain identical characteristics in gene expressions and multilineage differentiation capabilities. The invention has applications in the areas of cell culture, tissue transplantation, drug discovery, and gene therapy.

Figure 3D:
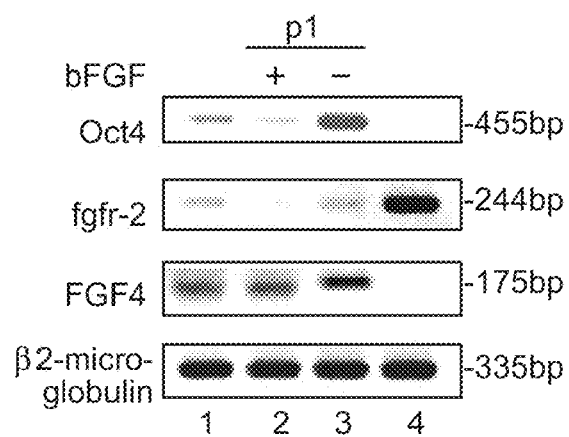

Next, it was aimed to identify the pluripotency of hTS cells in the culture. Oct4 is a transcription factor and a key determinant of pluripotency. Report states that Oct4 deficient embryos can still develop to the blastocyst stage, but the ICM cells are no longer pluripotent leading to apoptosis of the primordial germ cells rather than to differentiation into a trophectodermal lineage (J. Kehler et al., EMBO Rep., 5, 1078 (2004)). Instead, the ICM cells are restricted to differentiation along the extraembryonic trophoblast lineage (J. Nicholas et al., Cell, 95, 379 (1998)). Other researches suggest human (B. Gerami-Naini et al., Endocrinology, 145, 1517 (2004)) and mouse (J. Rossant, Stem Cells, 19, 477 (2001)) embryonic stem cells can be switched towards the trophoblast lineage by changing culture conditions and altering expression levels of Oct4. This leads to an interesting hypothesis that a formula of Oct4ON=ES, Oct4 OFF=TS might play a key genetic switch (J. Rossant, Stem Cells, 19, 477 (2001)). Moreover, treatment to blastocyst outgrowths with fibroblast growth factor 4 (FGF4) can increase the number of outgrowing trophectoderm cells (N. Chai et al., Dev. Biol., 198, 105 (1998)). Several related gene expressions including Oct4, fgfr-2, and FGF4 in the hTS cells were investigated by RT-PCR. The hTS cell culture (PV 07 cell line) in passage 6 displayed Oct4, fgfr-2, and FGF4 expressions (FIG. 3d). However, only the fgfr-2 expression was detected in the term placental tissues, but not Oct4 and FGF4. By adding bFGF to the hTS cells, the Oct4 and fgfr-2 expressions could be knockdown, indicating the involvement of bFGF in the gene switch regulation for stem cell differentiation.

Example 5

Animal Model of Pakinsonism and hTS Cells Transplantation

Immunocytochemical Analyses for TH Assays:
Paraformaldehyde (4%) fixed cells incubated in 0.1M PBS at 4° C. overnight after washing with PBS. After incubation with blocking solution (50 ml 0.1 M PBS, 0.05 g sodium azide, 1% horse serum, and 10% Triton X-100) for 1 h at room temperature, the cells were washed again. Cells were added with primary antibody (Sigma): TH-2 (1:200 dilution) or TH-16 (1:200 dilution) for 2 h and washed with PBS. After incubation with anti-mouse IgG with FITC or PE (Sigma) for 1 h, cells were thoroughly washed with PBS and subjected to immunofluorescence assay.

Transfection of hTS Cells Using F1B-GFP Reporter Plasmid:
F1B-GFP reporter plasmid was supplied by Dr. Chiu, I. M. Briefly, cultured hTS cells were co-transfected in a DNA mixture of F1B-GFP and pSV2neo (10:1 ratio, 50 µl in total). This DNA mixture was added slowly into 100 µL DOTAP solution containing 30 µL DOTAP Liposomal transfection reagent (Roche Applied Science, Indianapolis, Ind.) and 70 µl HBS (Gibco, 867 g HaCl in 80 ml Milli Q water+2 ml 1M HEPES solution, pH 7.4, at 4° C.) for 15 min at room temperature. The hTS cells, washed by PBS, were mixed well with the DNA mixture. After 24 h incubation, the stable cells lines were obtained by selection with G418 (400 µg/ml) (Roche Applied Science) through culture for 2-3 weeks until the colonies were formed. The G418-resistant cells were pooled and lysed. The cell lysates were analyzed by Western blotting using monoclonal anti-GFP antibody (Stratagene, La Jolla, Calif.) to quantitate the percentage of transfectants that express GFP. By subcultures, the transfected hTS cells were fixed with methanol (10 min) to detect the expression of GFP in hTS cell transfectants by immunofluorescence. The transfection rate in the present study yielded over 95%.

Rat Model of Parkinsonism and hTS Cells Transplantation
Sprague-Dawley rats (250-350 g) are used in models for 6-OHDA-lesioned hemiparkinsonism (PD). The protocol was approved by the Hospital Ethical Committee of National Taiwan University Hospital. The surgical procedures were described previously. Briefly, after anesthesia by cholral hydrate (4%, 1 cc/100 gm of body weight), stereotaxic lesions were carried out by infusion of 6-hydroxydopamine (Sigma) into the right median forebrain bundle (AP 2.8/Lat 2.2/Dep 8.0 mm) at a rate of 1 µg/0.5 µl/min for 8 min (injection pump: CMA 100). After 10 min, the tube was removed. Two weeks later, apormorphine-induced rotation tests (25 mg/kg, s.c.) were performed 20 min after cells transplantation. The turning rotations were recorded. Rotations of more than 25 in 5 min were included in the study. Analysis was set at 0, 3, 6, 9, and 12 weeks. Rats were separated into 3 groups: group a was injected with non-induced but plasmid-transfected hTS cells; group b with both plasmid-transfected and induced hTS cells; and group c with PBS injection as control. Cells were transplanted into 2 sites (each site: $3\times10^6$/4 µl) within the right unilateral striatum (1st site: AP+1/Lat+2.7/Dep 6.4 mm; $2^{nd}$ site: AP+0/Lat+2.7/Dep 6.4 mm).

The functional assessment in vivo was done to test whether the hTS cell-derived neural stem cells play a role in Parkinson's disease (PD). The F1B-GFP reporter plasmid transfected hTS cells were prepared with a yield of over 95% (FIG. 4a). Using a specific monoclonal antibody for tyrosine hydroxylase-2 or -16 detection, we observed immunocytochemically the expressions of TH-2 in the induced neural stem cells with a yield >95% (FIG. 4b) and TH-16 in the F1B-FGP reporter plasmid transfected hTS cells, with also a yield of >95%, after induction (FIG. 4c, d, e). Animal models of PD are popularly used to assess the effects of neural grafts implanted into the striatum (Dunnett, S. B. & Bjorklund, Nature 399, A32-A39 (1999)) Thus, unilateral injections of 6-OHDA into median forebrain bundle in rats (FIG. 4f, g, h, upper panel) permanently damaged all dopaminergic neurons in the SN pars compacta (snc) (Iancu, R. et al., Behav Brain Res 162, 1-10 (2005)) (FIG. 4f, g, lower panel). Two weeks later, we implanted both induced and non-induced transfected hTS cells (FIG. 4g; FIG. 4h) into the intrastriatal region. Phosphate buffer solution was used in the control group (FIG. 4f). Apomorphine-induced rotations were measured as described previously. The results demonstrated that the total number of contralateral rotations decreased significantly following the transplantation of non-induced hTS cells (FIG. 4k), and finally reduced to the baseline (25 turns/5 min) at 12 weeks (Repeated-measure ANOVA test: p=0.001). In the retinoic acid-induced group, the best recovery time was shown at 6 weeks ($p<0.05$). However, no difference between the induced and the control groups was observed at 12 weeks. All rats were killed after 18 weeks. Sections of the rat brains were sent for TH immunohistochemistry, and they also underwent immunocytochemistry for transfected hTS cells in the nigrostriatal pathway. No TH immunoactivity was detected in the lesioned striatum and snc of the induced hTS cell group or the control groups (FIG. 4f, g). Of great importance is the unexpected finding that in the non-induced hTS cells group, TH immunoreactivities were found in both the lesioned striatum and snc regions (FIG. 4h). The appearance of both transfected hTS cells and TH immunoreactivities in the lesioned areas of striatum (FIG. 4i) and snc (FIG. 4j) provides direct evidence that the implanted hTS cells can not only differentiate into dopaminergic neurons in situ, in such a unique micro-environment, but also repair the function originally damaged by 6-OHDA-lesions. This goes against the accepted notion that 6-OHDA-induced lesions are permanent. On the contrary, the hTS cells are able to find the their way home along the nigrostriatal pathway by upstream migration, much as salmon find their way back up the river in nature. How this is achieved remains to be clarified. Our findings show that it is possible to use hTS cells as viable alternatives to hES and hEG cells, thereby circumventing the ethical dilemmas related to use of embryonic stem cells for human stem cell research and gene-based and cell-based therapies.

Example 6

(A) Methods of Differentiation of hTS Cells into Pancreatic β-Islet Like Cell

Human trophoblastic villi were obtained from the early ectopic pregnancy (6-8 weeks of gestation) at fallopian tube and human trophoblastic stem (hTS) cells were purified as described previously. For pancreatic β-islet cells differentiation, a two-step regimen was applied based on the characteristic glucose-stimulated insulin secretion (Wilcox G., Clin Biochem Rev., 2005; 26:19-39). Briefly, cells ($1.4 \times 10^5$) were pre-induced in basic DMEM medium (5.5 mM glucose, Gibco) containing 1 mM β-mercaptoethanol (Sigma), 10 mM nicotinamide (Sigma), namely LDMEM-mn, at 37° C. 5% $CO_2$ for 24 h. For further induction, cells were cultured in HDMEM medium (Gibco) containing 15 mM glucose, 1 mM β-mercaptoethanol, 10 mM nicotinamide, namely HDMEM-mn.

(B) Evidence of β-Islet-Like Cells Differentiated from the hTS Cells

Cells Culture

Prior to the induction, hTS cells ($1.4 \times 10^5$, PV 07, passage 5) were cultured in basic DMEM medium (Gibco) for two days to reach a stable status. The hTS cells appeared in an elongated spindle shape before pre-induction (FIG. 5a). Then, the culture medium was changed into LDMEM-mn for 24 h as pre-induction. Morphologically, the cells aggregated to from into variable multicystic formation at 6 h (FIG. 5b). The cells' morphology gradually changed from spindle shapes into rounded and/or oval shapes, and eventually toward several scattered grape-like clusters (FIG. 5c) after 24 h pre-induction. When the medium was switched into a hyperglycemic status, i.e., HDMEM-mn for 6 h, the isolated grape-shaped cells first appeared at 3 h. The clusters showed a trend to link with each other forming a network after 6 hours incubation (FIG. 5d). The 6 h induction was applied and attributed to the empirical fact that the hTS cells would die at 8-10 hours in such hyperglycemic conditions (20-22 mM). These cellular damages are probably attributed to the effect of glucotoxicity. The isolated grape-like clusters possibly demonstrate initial stages of pancreatic organogenesis. The results showed that the differentiated hTS cells possessed insulin secreting capability, exhibiting characteristic glucose-stimulated insulin secretion after an acute glucose bolus administration (FIG. 5h). Meanwhile, small amount of the culture medium (0.5 ml) was collected at several points during the culture and subjected for insulin determinations by radioimmunoassay using commercial kits per manufacturer's directions (Diagnostic Products Corp., Los Angeles, Calif.). The result displays a residual trace of insulin in the medium after the acute glucose bolus administration, which may reflect the secreting pattern previously observed in human pancreatic β-islet cells (Jose et al., The Journal of Physiology (1999), 520.2, pp. 473-483) that there are two intracellular pools of insulin, i.e., primed and reserved forms.

The cell culture medium was changed back to the basic DMEMS for culture for 18 h. We discovered that fibroblastic outgrowths appeared from the grape-like clusters as a result (FIG. 5e). The de-differentiation phenomena became obvious after 2-, and 4-days culture (FIG. 5f, g). The mechanism for de-differentiation is still unclear. The differentiation and de-differentiation in cellular morphology are unique and repeatable in the present study.

The findings offer the possibility of using hTS cells as a model in the study of not only the patterning of beta-cells in early pancreatic development, the signaling in differentiated beta-cells of the endocrine pancreas in regulating insulin production, but also the pathogenesis of the impaired placental function at molecular levels. In murine, it has been reported recently that parathyroid hormone-related protein can regulate cellular changes in secondary trophoblast giant cells, which invade into the uterus at implantation during differentiation (El-Hashash and Kimber, Dev. Biol. 2005 Dec. 19). The result implies that insulin may play a role in regulating the cellular changes during hTS cell differentiation and de-differentiation. Another report revealed that the Notch pathway plays as a mediator of beta-cell de-differentiation in type 1 diabetes mellitus that inhibited the differentiated functions in dividing but not in terminally differentiated beta-cells (Darville M I et al., Biochem Biophys Res Commun., 2006; 339:1063-8). The de-differentiation phenomenon of the hTS cells can possibly be used as a model for further research of the role of the Notch pathway in type 1 diabetes mellitus. Furthermore, cellular de-differentiation can induce anticancer activity that makes cells resistant to carcinogenesis (Scott R E et al., Differentiation., 2005; 73:294-302), though the molecular mechanism of this phenomenon has not been defined. The de-differentiation phenomenon of the hTS cells can also be applied to the study of the mechanism of cancer.

Figure 6:
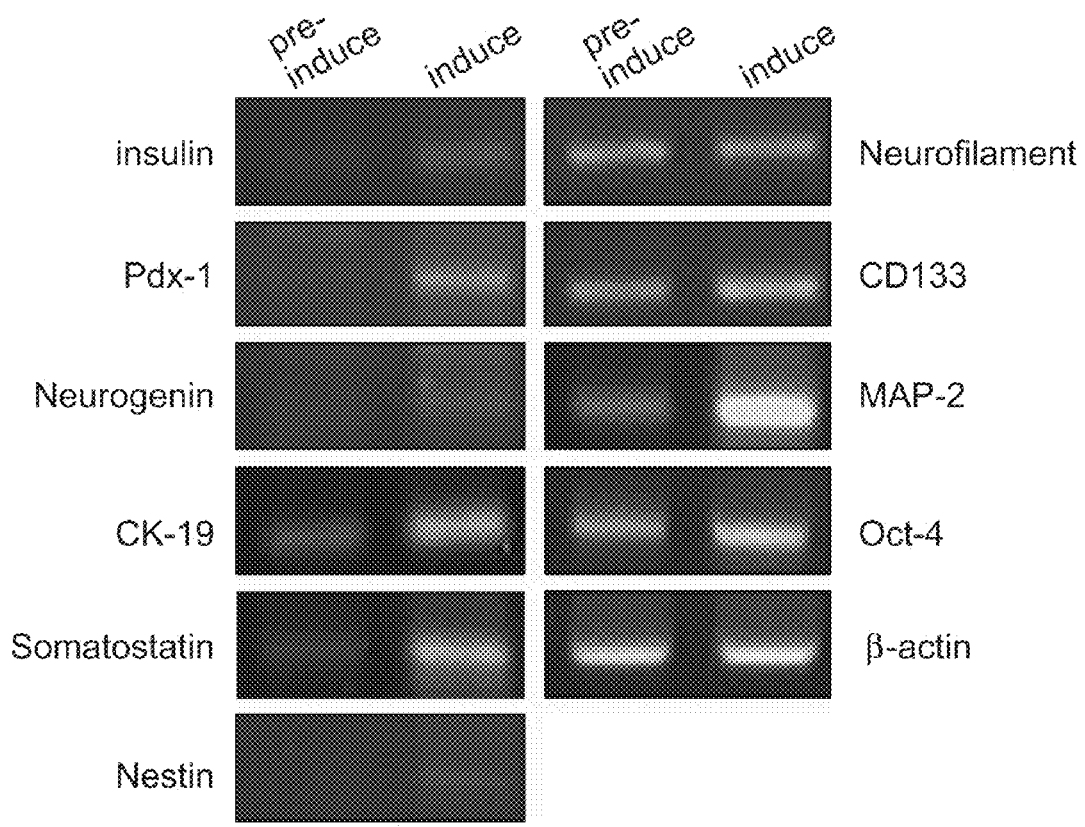
FIG. 6 shows insulin-related neuroendocrine components in non-drug-induced and drug-induced hTS cells shown in RT-PCR. The left-side of each column indicates pre-induced and right-side of each column indicates induction at 30 h.

GFAP (astrocyte-specific protein) and Oct-4 (transcription factor unique for cell proliferation). The results (FIG. 6) showed that insulin, Pdx-1, neurogenin and nestin expressions appeared after induction. Enhanced expressions of CK19, somatostatin, neurofilament, CD133, MAP-2, and Oct-4 were observed after drug induction in comparison with that of non-induced cells. However, GFAP and MPB did not express in this study. These results demonstrated that the differentiated islet-like cells possess most of the genetic expressions similar to human pancreatic islets as a complex neuroendocrine organ.

TABLE 3

Sequences of primers
(SEQ ID NOS 27-48, respectively, in order of appearance)

| Gene | Sequence (5'→3') | Product (bp) | Tm |
|---|---|---|---|
| Insulin | F: AGCCTTTGTGAACCAACACC<br>R: CTCACCCTGCAGGTCCTCT | 104 | 60.8 |
| Pdx1 | F: GTCCTGGAGGAGCCCAAC<br>R: GCAGTCCTGCTCAGGCTC | 360 | 58 |
| Somatostatin | F: CAGGAACTGGCCAAGTAC<br>R: AGTTCTTGCAGCCAGCTTTG | 186 | 54.6 |
| CK19 | F: GCCTCCAAGGTCCTCTGAG<br>R: GGCAGGTCAGGAGAAGAGC | 120 | 63.5 |
| Neurogenin | F: ACTACATCTGGGCGCTGACT<br>R: GGGAGACTGGGGAGTAGAGG | 144 | 58.1 |
| Neurofilament | F: TGGGAAATGGCTCGTCATTT<br>R: CTTCATCCAAGCGGCCAATT | 332 | 55.5 |
| Nestin | F: CTCTGACCTGTCAGAAGAAT<br>R: GACGCTGACACTTACACAAT | 315 | 51.8 |
| CD133 | F: GAGCGCAAAGACTACCTGAAGA<br>R: CGACTCTAGCTCGATGCTCTTG | 230 | 57 |
| MAP-2 | F: GCATGAGCTCTTGGCAGG<br>R: CCAATTGAACCCAGTAAAGCC | 192 | 55.4 |
| β-actin | F: GTGGGGCGCCCCAGGCACCA<br>R: CTCCTTAATGTCACGCACCATTTC | 539 | 55.5 |
| Oct-4 | F: GGAAAGGCTTCCCCCTCAGGGAAAGG<br>R: AAGAACATGTGTAAGCTGCGGCCC | 450 | 64 |

Insulin-Related Gene Expressions in the Derived β-Islet-Like Cells

To further identify the similarity with human pancreatic β-islet cells in biological characteristics, the harvested differentiated hTS cells were examined by genetic expressions in relation to pancreatic neuroendocrine activities using RT-PCR. The primer sequences used were shown in Table 3.

The methods used were described previously in this context. The investigations included insulin (expressed by β-islet cells), Pdx-1 (transcription factor expressed by β-islet cells), somatostatin (expressed by delta-islet cells), CK19 (progenitors of islet and ductal cells), neurogenin (involved in neurogenesis, also a common precursor of the 4 pancreatic endocrine cell types), neurofilament (structural protein for neuron), nestin (intermediate filament structure protein), CD133 (identified neural stem cells with rising to neuron and glial cells), MAP-2 (dendrite-specific protein), MPB (myelin sheath surrounding protein produced by oligodendrocytes), Immunocytochemistry of the Insulin-Related Proteins in the β-Islet-Like Cells To further verify this notion, the differentiated hTS cells were plated in six-well chamber slides and cultured at 37° C. with humidity at 5% $CO_2$ for 24 h. After cells adhered to the slide, immunocytochemical study was performed. The cells were washed with phosphate-buffered saline (PBS), fixed in 4% paraformaldehyde at 4° C. overnight and permeabilized with 0.4% Triton X-100 for 20 min. To reduce non-specific antibody binding, cells were first pre-incubated with a blocking buffer (10% BSA in PBS) for 20 minutes before incubation with primary antibodies. A goat anti-insulin (1:100 dilution, Santa Cruz), a rabbit anti-glucagon (1:50 dilution, Santa Cruz), a goat anti-IGF1 (1:50 dilution, Santa Cruz), a mouse anti-tau (1:50 dilution, Santa Cruz), a goat anti-MAP-2 (1:50 dilution, Santa Cruz), and a goat anti-amylase (1:50 dilution, Santa Cruz) were applied for 60 min. After washing with PBS-Tween 20 buffer for 5 min three times each, secondary anti-goat IgG Texas red-conjugated antibody (1:500, dilution, Santa Cruz) and anti-rabbit IgG FITC-conjugated antibody (1:500 dilution, Santa Cruz), anti-goat IgG FITC-conjugated antibody (1:500, dilution, Santa Cruz) and anti-mouse IgG FITC-conjugated antibody (1:500, dilution, Santa Cruz) were applied for 60 min. After washing with PBS-Tween 20 buffer for 5 min three times, the cells were counterstained with 100 ng/ml DAPI (Sigma) for 10 min to identify the nucleus. The immunoreactivities were analyzed by using a fluorescent microscope (Provis, Olympus). The results confirmed that hTS cells can differentiate into pancreatic islet-like cells with positive immunoreactive expressions of insulin, insulin-like growth factor-1 (IGF-1), glucagon, amylase, tau and MAP-2 (FIG. 7).

Figure 8:
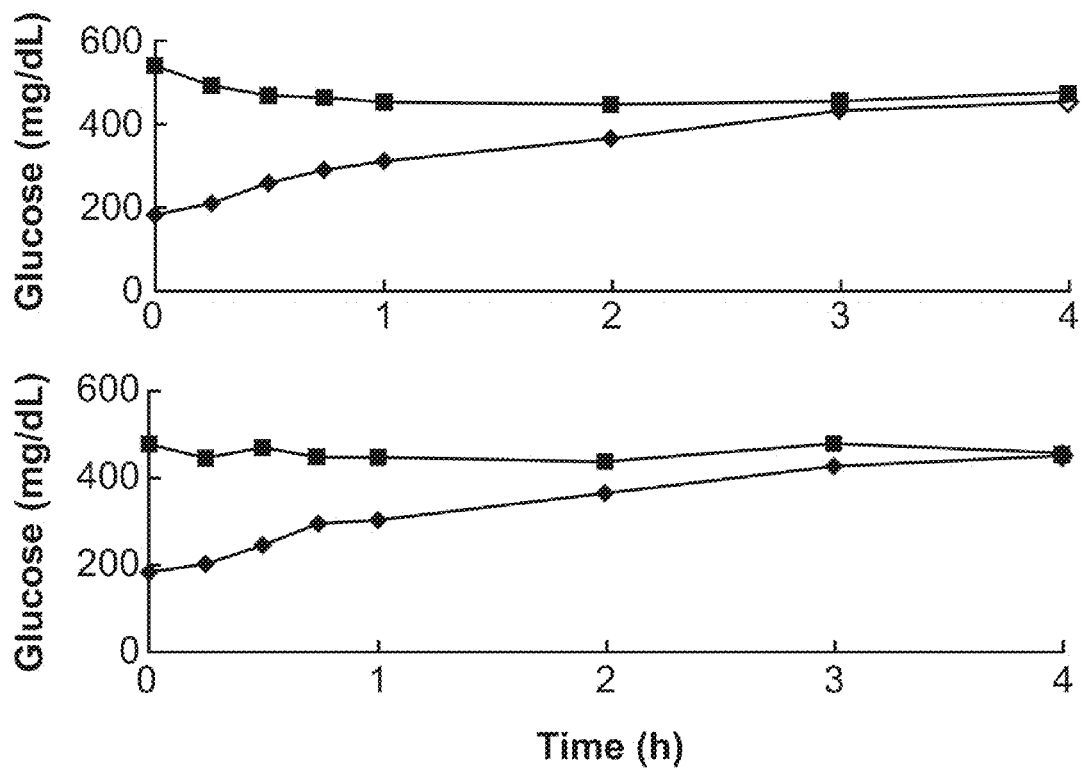
FIG. 8 shows glucose equilibrium in the Transwell dish with hTS cells implantation. (a) indicating the drug-induced hTS cells and (b) indicating non-drug-induced control. (c) arrow indicates a 7 mm 3-D cellular mass on the collagen matrix.
Figure 8:
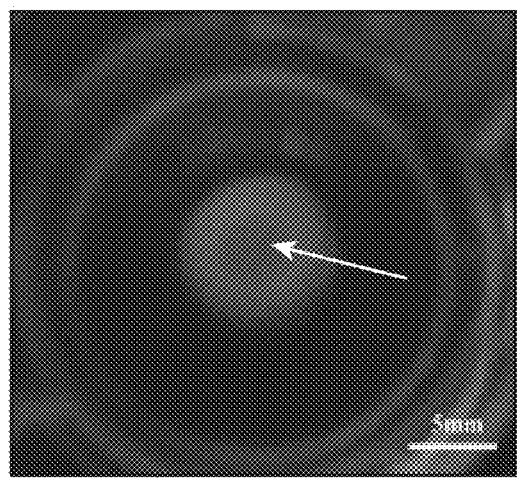

(C) Establishment of 3-D Pancreatic β-Islet Tissues Using a Collagen Model In Vitro Based on the morphological observations during cell culture, we became aware of the fact that sudden changes from the low (5.5 mM) to high (15 mM) glucose levels probably resulted in stress to the hTS cells. To avoid this side-effect, we applied a culture system using mixed collagen gels as matrices in a Transwell dish (Corning Incorp., Corning, N.Y.) for two reasons: one is to explore hTS cells' invasive capability during proliferation and the other is to find out the possibility of promoting pancreatic islet-like tissue growth on the gel matrix during induction. Thus, collagen mixtures of vitrogen collagen (1:5 dilution, Cohesion, Palo Alto. CA) and collagen from rat tail (3 mg/ml of buffer solution, c7661, Sigma) at a ratio of 1:1 (v/w) in acidic solution (0.012 N HCl) were prepared and coated (1.5 ml) onto the upper chamber of the Transwell dish for 20-30 min form a gel layer. For testing, HDMEN-mn medium (18 mM glucose) was placed in the lower chamber of the Transwell dish (2.4 cm diameter, 0.4 µm pore size), while LDMEN-mn (5.5 mM glucose) was placed in the upper chamber. For pre-test, the equilibrium of glucose concentration was achieved at a level around 455 mg/dl at 4 h test. Thus, we implanted the induced and non-induced hTS cells ($5\times10^5$ cells) on the collagen gel and transferred to the Transwell described as above for examination. The drug induced hTS cells (FIG. 8a) and the non-drug-induced control (FIG. 8b) both achieved equilibrium of glucose levels at 4 h. Both cell-embedded collagen mixtures formed a 3-D cellular mass (FIG. 8c). Both culture mediums were collected and insulin level was determined by radioimmunoassays. Each gel mass was fixed in 4% paraformaldehyde overnight at 4° C. and subjected for insulin immunohistochemistry.

Histologically, in the non-drug-induced control gel mass, proliferation of spindle cells showing hyperchromatic nuclei and presence of nucleoli as well as cytoplasmic vacuoles, revealed an immature feature around 10 cell-layers with rich extra-cellular matrices and stratification in thin, sheet-like appearance (FIG. 9a). The cells appear vertically arranged. The surface appeared in a flat, umbrella-like layer. The cells in the middle zone were randomly and irregularly arranged. The cells in the lower zone towards the collagen showed vertical formations, indicating penetration into the collagen.

However, in the gel mass of the drug-induced hTS cells, the cell components became more compact and well-differentiated, evidenced by the reduced cytoplasmic vacuoles and the amount of cellular matrix (FIG. 9b). The mechanism for this 3-D formation is unclear. However, recent research revealed that insulin-like growth factor-1 can stimulate lamellipodia formation and promote adhesion of trophoblast cells to extracellular matrix by activating their adhesion molecules that must be activated within the implantation window (Kabir-Salmani et al., 2002). In this study, immunoreactive insulin levels in the total culture medium were measured by radioimmunoassays with a range of 15-27 mIU/ml.

Immunohistochemically, no insulin-staining granules were visible in the cytoplasm of the cells in the non-drug-induced hTS cells (FIG. 9c). However, it expressed apparently in the drug-induced hTS cells (FIG. 9d). Tissues from normal pancreas (FIG. 9e) and insulinoma (FIG. 5f) were obtained and used as positive control. More importantly, this fact provides evidence that the hTS cells are able to form pancreatic islet-like tissues in vitro, suggesting the possibility to produce pancreatic β-islet tissues for future clinical applications in humans with type 1 diabetes mellitus.

Evidence was found that hTS cells may differentiate into pancreatic islet-like cells with insulin-secreting capability. The unique biological characteristics of hTS cells in differentiation and de-differentiation in combination with the present 3-D cellular model might be used as platforms for: (1) the research for understanding the mechanisms in any differentiated cell phenotypes. For example, research in pancreatic development of type 1 diabetes mellitus, evaluating the effects of drugs in early embryonic implantation, development of placental functions in relation to placental insufficiency, gestational diabetes mellitus, macrosomnia, early pregnancy loss, genetic abnormalities, and choriocarcinoma; and (2) the establishment of pancreatic tissues and/or organs which may one day help to provide a source of islets for use in transplantation therapy to treat type 1 diabetes.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of differentiating an isolated human trophoblast stem cell into a neuron, the method comprising:

administering said human trophoblast stem cell to the striatum region of the brain of a mammal, wherein said human trophoblast stem cell differentiates into a neuron, and wherein said human trophoblast stem cell expresses transcripts for SSEA-1, SSEA-3, SSEA-4, and Oct4, and is isolated from trophoblast tissue.

2. The method of claim 1, wherein said neuron is a dopaminergic neuron.

3. The method of claim 1, wherein said stem cell is pre-induced with an all trans-retinoic acid prior to said administering.

4. The method of claim 1, wherein said stem cell is not pre-induced with an induction drug prior to said administering.

5. The method of claim 1, wherein said brain of said mammal is damaged or suffered neuronal loss, prior to said administering.

6. The method of claim 5, wherein said damage is to a dopaminergic neuron.

7. The method of claim 5, wherein said neuronal loss is to a dopaminergic neuron.

8. The method of claim 1, wherein said stem cell is transfected with an expression vector.

9. The method of claim 1 wherein the stem cell, after being administered to said mammal, extends processes into the substantia nigra pars compacta (SNc) region of said brain of said mammal.

10. The method of claim 1 further comprises administering to the mammal an effective amount of a therapeutic compound.

11. The method of claim 10, wherein the therapeutic compound is a drug, a chemical, or an antibody.

12. The method of claim 1 further comprises administering to the mammal an effective amount of a compound that modulates bFGF, Oct 4, FGFR-2 or FGF4 expression, in said stem cell.

13. The method of claim 12, wherein the compound is an inhibitor of bFGF, Oct 4, FGFR-2 or FGF4.

14. The method of claim 1, wherein the mammal is a human.

15. The method of claim 1, wherein the administering is via injection, transplantation, or surgical operation.

* * * * *

SEQUENCE LISTING

<160> NUMBER OF SEQ ID NOS: 48

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctaggcatca cctgtgccat acc                                              23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagtgaccag ttcatcagat tcatc                                            25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcagccacc gagacaccat                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggcaagggc aagggggaaga                                                 20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catagagacc gtcacagcaa g                                                21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

-continued

```
atgaacacca cactgacaac c                                               21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acggcgagaa gggagaagtt g                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggggtccag ggttgccatt g                                               21

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 agcgcccct cgtgtatg                                                    18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgtccccggc aacttcagc                                                  19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cggcggcgga actgctacga a                                               21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

-continued ggggcggggg cggaaactt                                              19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctgttatgg gtgaaactct g                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ataaggtgga gatgcaggct c                                           21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtcacccaa gcaacaaagt                                             20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctcctgcgt tcaagtcatc                                             20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtcctggagg agcccaac                                               18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcagtcctgc tcaggctc                                               18

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 19
ggaaaggctt ccccctcagg gaaagg                                        26

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 20
aagaacatgt gtaagctgcg gccc                                          24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 21
ggaggggatg tggagtttgt                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 22
actggttggc ctgccctata                                               20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 23
agcgaggcgt ggtgagcatc tt                                            22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 24
tggtccgccc gttcttactg ag                                            22

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctcgcgctac tctctctctt tctgg                                          25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcttacatgt ctcgatccca cttaa                                          25

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agcctttgtg aaccaacacc                                                20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctcaccctgc aggtcctct                                                 19

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtcctggagg agcccaac                                                  18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcagtcctgc tcaggctc                                                  18

```
<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caggaactgg ccaagtac                                                 18

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agttcttgca gccagctttg                                               20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcctccaagg tcctctgag                                                19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggcaggtcag gagaagagc                                                19

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
actacatctg ggcgctgact                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gggagactgg ggagtagagg                                               20

<210> SEQ ID NO 37
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgggaaatgg ctcgtcattt                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cttcatggaa gcggccaatt                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctctgacctg tcagaagaat                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gacgctgaca cttacagaat                                              20

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagcgcaaag actacctgaa ga                                           22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgactctagc tcgatgctct tg                                           22

<210> SEQ ID NO 43
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcatgagctc ttggcagg                                                     18

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccaattgaac ccagtaaagc c                                                 21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtggggcgcc ccaggcacca                                                   20

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctccttaatg tcacgcacga tttc                                              24

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaaaggctt ccccctcagg gaaagg                                            26

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aagaacatgt gtaagctgcg gccc                                              24
```